(12) United States Patent
Taparia

(10) Patent No.: US 11,969,377 B2
(45) Date of Patent: Apr. 30, 2024

(54) SINGLE-USE INSTRUMENT TO PREPARE AND SAFELY PLACE AN INTRA-UTERINE DEVICE

(71) Applicant: PREGNA INTERNATIONAL LIMITED, Mumbai (IN)

(72) Inventor: Mukul Taparia, Mumbai (IN)

( * ) Notice: Subject to any disclaimer, the term of this patent is extended or adjusted under 35 U.S.C. 154(b) by 128 days.

(21) Appl. No.: 17/536,026

(22) Filed: Dec. 14, 2021

(65) Prior Publication Data

US 2023/0127093 A1 Apr. 27, 2023

(30) Foreign Application Priority Data

Oct. 27, 2021 (IN) .............................. 202121049195

(51) Int. Cl.
 *A61F 6/12* (2006.01)
 *A61F 6/18* (2006.01)

(52) U.S. Cl.
 CPC ...................................... *A61F 6/18* (2013.01)

(58) Field of Classification Search
 None
 See application file for complete search history.

(56) References Cited

U.S. PATENT DOCUMENTS

| | | | |
|---|---|---|---|
| 3,783,861 A | 1/1974 | Abramson | |
| 4,143,656 A | 3/1979 | Holmes | |
| 5,785,053 A | 7/1998 | MacAndrew et al. | |
| 9,265,651 B2 * | 2/2016 | Pandit | A61F 6/18 |
| 10,028,858 B2 | 7/2018 | Deckman et al. | |
| 2013/0014762 A1 | 1/2013 | Deckman et al. | |
| 2018/0055684 A1 | 3/2018 | Lad et al. | |
| 2018/0207023 A1 | 7/2018 | Mehra et al. | |
| 2019/0307600 A1 | 10/2019 | Deckman et al. | |
| 2022/0087856 A1 * | 3/2022 | Taparia | A61F 6/14 |

FOREIGN PATENT DOCUMENTS

IN 273975 10/2008

OTHER PUBLICATIONS

U.S. Appl. No. 15/745,579, filed Jul. 26, 2018, Pregna International Ltd.

* cited by examiner

*Primary Examiner* — Camtu T Nguyen
(74) *Attorney, Agent, or Firm* — Ifica D. Mehra

(57) ABSTRACT

An instrument (10) to downfold an intrauterine device (30), comprising a base (20) with a delatcher (26); a navigator (50) having an aligner plug (51A), a slot (56); an open converger (40) having a flange (45), a covered channel (41); a driver assembly (60) having a bidirectional carrier (61), a graduated tube (71), and a latching rod (81); and a gated support (90) having a leafy arm (91) and a downward fork (94) forming an inverted "U" gate (95) having sloped edges (97) with end points (96), at the other end, a holder (92) having an elongated grip (93) on either side; wherein a lower end (37) of the stem (33) of IUD (30) sits on a conical seat (82) having two resting points (83) on the latching rod (81), while a knot (38) of the string (31) sits in the knot room (84) on the latching rod (81).

13 Claims, 38 Drawing Sheets

SINGLE-USE INSTRUMENT TO PREPARE AND SAFELY PLACE AN INTRA-UTERINE DEVICE

FIELD OF THE INVENTION

The present invention relates to an intra-uterine device, particularly to an instrument which is to load and insert the intra-uterine device and the process of loading, inserting and safely placing the intra-uterine device in the uterus of a woman, hygienically.

BACKGROUND OF THE INVENTION

There are several female contraceptives available. An intra-uterine device (herein after abbreviated as (IUD) is a long-term or medium-term contraceptive which is placed in the uterus of female.

The IUDs cannot be inserted in uterus in their original shape and form as the opening of the cervix is small. For this reason, all IUDs use an insertion instrument for folding, insertion and proper location of the IUD. U.S. Pat. No. 3,783,861 discloses an inserter utilized to insert an intra-uterine device (IUD) having a first horizontally disposed arm and a second arm, substantially transverse thereto, coplanar therewith, and depending therefrom. This IUD folds with one arm up and the other arm down, in substantially in a straight line. This IUD is not what is a commonly known "Copper T".

Deriving the common name "copper T" from their shape, the two arms forming "T" of such IUDs are generally folded either upwards or downwards so that IUD can be contained in the opening of a narrow tube/inserter which then can be inserted in the uterus. This process of folding the IUD so that the instrument/inserter is ready to insert is known as loading or preparing the IUD.

Loading or preparing of IUD needs to be done minutes before it is required to be inserted in uterus, and if done earlier, or if supplied duly loaded, then the IUD shall not return to the desired "T" shape in uterus and shall not work effectively. Due to this requirement, the process of loading has to be performed by service providers just prior to inserting and placing IUD in uterus.

Up-folding IUDs and down-folding IUD have a significant difference in their preparation and placement procedure. Upfolding IUDs implies that arms forming "T" are together while stem of IUD is below folded arms. This may be easily understood from FIGS. 1A to 3B of U.S. Pat. No. 5,785,053A. Patent application US2013/0014762(A1) also comprehensively covers an upfolding IUD. Down-folding implies that arms forming "T" as well as stem of IUD are together. This may be easily understood from FIGS. 7 and 9 of U.S. Pat. No. 4,143,656.

There is a significant difference in process of inserting and placing an up-folding IUD and a down-folding IUD in uterus. While placing an upfolding IUD, the arms of the "T" start unfolding downwards as soon as IUD is made to gradually eject out of the instrument. Person placing such upfolding IUD takes a pause to allow the upfolding arms to unfold at their own pace before finally placing IUD in uterus, lest ends of arms of IUD gets entangled with side walls of uterus, preventing a far end of IUD to reach fundus! On the other hand, when placing a downfolding IUD, there is no such precaution needed as the arms of IUD unfold upwards at their own natural pace while a far end of the IUD touches fundus.

In other words, an upfolding IUD is easier to load and difficult to place in uterus, while a downfolding IUD is relatively more difficult to load and relatively easier to place.

U.S. patent application Ser. No. 15/745,579 discloses an instrument to load a downfold IUD without human maneuvering. US 2018/0055684 A1, on the other hand discloses another instrument suitable for upfolding IUDs.

Prior art like U.S. Ser. No. 10/028,858, US2019/0307600 continue to ignore that a string attached to the IUD substantially stays in the instrument when the IUD is just placed in the uterus and the instrument is being withdrawn. Therefore, string entangling in the instrument remains a potential cause of disturbing safe placement of IUD in the uterus.

Such instruments being for one-time use, hygiene and prevention of re-use are important factors.

Present invention effectively and economically addresses hygienic loading or preparation of downfolding IUDs for insertion and safe placement in uterus.

OBJECTIVES

The objective is to invent an instrument to load or prepare an intra-uterine device hygienically.

Another objective is to invent a simple instrument to load or prepare an intra-uterine device which is downfoldable.

Yet another objective is to invent an instrument which is capable of loading the intra uterine device in a consistent manner.

Yet another objective is to invent an instrument that causes minimal trauma to woman.

Yet another objective is to invent an instrument that ensures a horizontal orientation of the IUD, while the instrument may operate from an either horizontal orientation.

Yet another objective is to ensure suture release mechanism that ensures that the suture/thread/string is never stuck anywhere after deployment.

Yet another objective is to ensure single hand operation for insertion, deployment and retraction steps of the instrument.

Yet another objective is to ensure prevention of accident or injury during insertion in any case to avoid perforation of fundus.

Yet another objective is to invent an instrument which is easily destroyable to prevent multiple use.

Yet another objective is to achieve multiple stages of complete process with a single hand and knob movement.

Yet another objective is to eliminate and or minimize the guesswork of the user in complete operation while preparing/loading, deployment/release.

Yet another objective is to prepare string length prior to insertion, according to uterus size of woman.

SUMMARY OF INVENTION

It is to be particularly noted that a downfolding and an upfolding of a T-shaped IUD are entirely different processes and consequently no prior art instrument, and NOT even the instrument as per present invention can be interchangeably used for upfolding and downfolding IUDs without major constructional differences.

The instrument according to present invention comprises a down foldable "T" shaped intra-uterine device (IUD), a base, a navigator, an open converger, a driver assembly, a gated support.

The preferred embodiment is around the IUD generally comprising a frame having two identical arms on either side of a stem, with both arms of the IUD foldable towards the stem of the IUD. The instrument is shipped when the IUD is with its arms in a "T" formation with respect to the stem, as it should be when placed in uterus of woman. The arms are in a shrunk formation while inserting in uterus, and in an interim downwards formation in the course of preparation for insertion. The IUD further comprises a contraceptive material disposed around the stem, and at least one string emerges from a lower end of the stem, generally via a knot. The string has a terminating ends. The terminating ends of the string are concealed in the instrument.

As shall be evident, the process of loading, inserting in uterus and safely releasing the IUD is carried out by a single hand operation—carrying the instrument between fingers and thumb, and it is of great benefit to the medical service provider.

There is provided a string management arrangement involving a graduated tube, the strings of the IUD and the base. In the preferred embodiment, the string management arrangement is disposed on the floor of the base. There is provided at least one outpoint and one inpoint on the floor of the base. The string exits from the outpoint and re-enters from the inpoint. The string is accessible to the medical service provider between the outpoint and the inpoint and the medical service provider has a preferred option to trim the string as per sounding measurement of uterus of woman, BEFORE inserting the graduated tube in the cervix thereby avoiding use of scissors or cutting tool inside vaginal cavity, and this is most desired, safer and therefore preferred way of using the instrument as per the present invention. The outpoint is at a trim length which corresponds to a minimum recommended excess string length expected to be hanging outside cervical os in vaginal cavity of woman. The inpoint is at a conservative length.

Medical service provider has the freedom to trim the string anywhere within the conservative length. A scale is provided alongside to facilitate precision in trimming.

The open converger has a flange towards the IUD end, a covered channel commencing with a circular opening and transitioning gradually to a funneling opening towards the operator end, the covered channel being symmetrical about an imaginary plane passing through a line X-X' and orthogonal to this paper. The covered channel has an additional room towards an upper side. The funneling opening diverges to two dome shaped openings on either side of the open converger. The open converger is preferably made of a tough, transparent and virgin engineering thermoplastic.

The driver assembly comprises a bidirectional carrier, a graduated tube, and a latching rod.

The gated support has a leafy arm having a holder at one end, and a downward fork forming an inverted "U" gate having sloped edges with end points, at the other end. The holder has an elongated grip on either side. The leafy arm acts as a leaf spring which returnably lifts up. The navigator has an aligner plug at its IUD end.

Any IUD placed properly in uterus of a woman ought to sit closest to fundus of uterus, and strings ought to be long enough to hang out of the cervical os by a check length about 3 to 5 cm, so that while woman can just feel presence of IUD by feeling its strings by inserting her finger(s) in her uterus, the string(s) should not cause discomfort to her partner during intercourse. A uterine depth, that is a measure from fundus to cervical os of different woman illustratively varies between 4 cm to 10 cm. IUD supplied with the instrument as per present invention has a string long enough to meet the medical requirement described above for all sizes, and excess length of string is trimmed away during or after insertion and placement of IUD in uterus. Before starting insertion procedure, the medical service providers measure a uterine depth by known methods.

A method to load the instrument as per present invention and safely place the IUD in uterus comprises the steps of:

a) Sounding a uterus of woman and determining a uterine depth, b) Sliding the bidirectional carrier towards the IUD end by medical service provider placing his or her thumb on the push zone and applying a forward force $F_f$ on the cliff, the graduated tube along with the latching rod pushing the lower end of the stem of the IUD, the inverted "U" gate supporting the stem from both sides and preventing a buckling of the stem of the IUD, and the arms of the IUD folding down, c) Further sliding the bidirectional carrier towards the IUD end by medical service provider continuing placing his or thumb on the push zone and further applying the forward force $F_f$ on the cliff, the downward projection of the latching rod getting obstructed by the delatcher on the base, resultantly the pair of locking teeth of the bidirectional carrier getting delatched from the second pair of seats and getting latched with the first pair of seats of the latching rod, the edge of the graduated tube pushing up the slope, lifting up of the inverted "U" gate, sliding of only the graduated tube onto the stem by the measure of length, and engulfing a part of arms of the IUD, d) Further sliding the bidirectional carrier towards the IUD end by medical service provider continuing placing his or thumb on the push zone and further applying the forward force $F_f$ on the cliff, the graduated tube along with the latching rod push the lower end of the stem of the IUD till the graduated tube with a folded IUD emerges out from the flange by the measure of the uterine depth, e) Trimming the string in-between the outpoint and the inpoint of the instrument, f) Sliding backward the bidirectional carrier towards the operator end by the medical service provider placing his or thumb on the push back zone and applying a backward force Fb on the cliff, pulling back the graduated tube along with the latching rod from over the stem of the IUD, g) Applying a force (Fbr) by thumb on the open converger, separating a part of the base carrying the open converger, rendering the instrument non-reusable irreversibly.

The step (f) is performed after inserting the graduated tube in the uterus till the flange touches the cervical os, thereby releasing the IUD in the uterus with the arms of the IUD next to fundus. Step (g) is performed after withdrawing the instrument from vaginal cavity of woman.

BRIEF DESCRIPTION OF DRAWINGS

FIG. 3 shows different folded position of an IUD which the instrument as per present invention is suitable for.

DETAILED DESCRIPTION OF INVENTION

The present invention of an instrument to load and insert a downfoldable intra-uterine device and process thereof will now be described with reference to the accompanying drawings. It is to be understood that the description explains the preferred embodiments and several ways are possible around the invention. Apropos, the description should not be construed to limit the invention in any way whatsoever. The terms and expressions which have been used here are merely for description and not for limitation. The term "preparing" and "loading" are used interchangeably.

It is to be particularly noted that a downfolding and an upfolding of a T-shaped IUD are entirely different processes and consequently, no prior art instrument, and NOT even the instrument as per present invention can be interchangeably used for upfolding and downfolding IUDs without major constructional differences.

Figure 1:
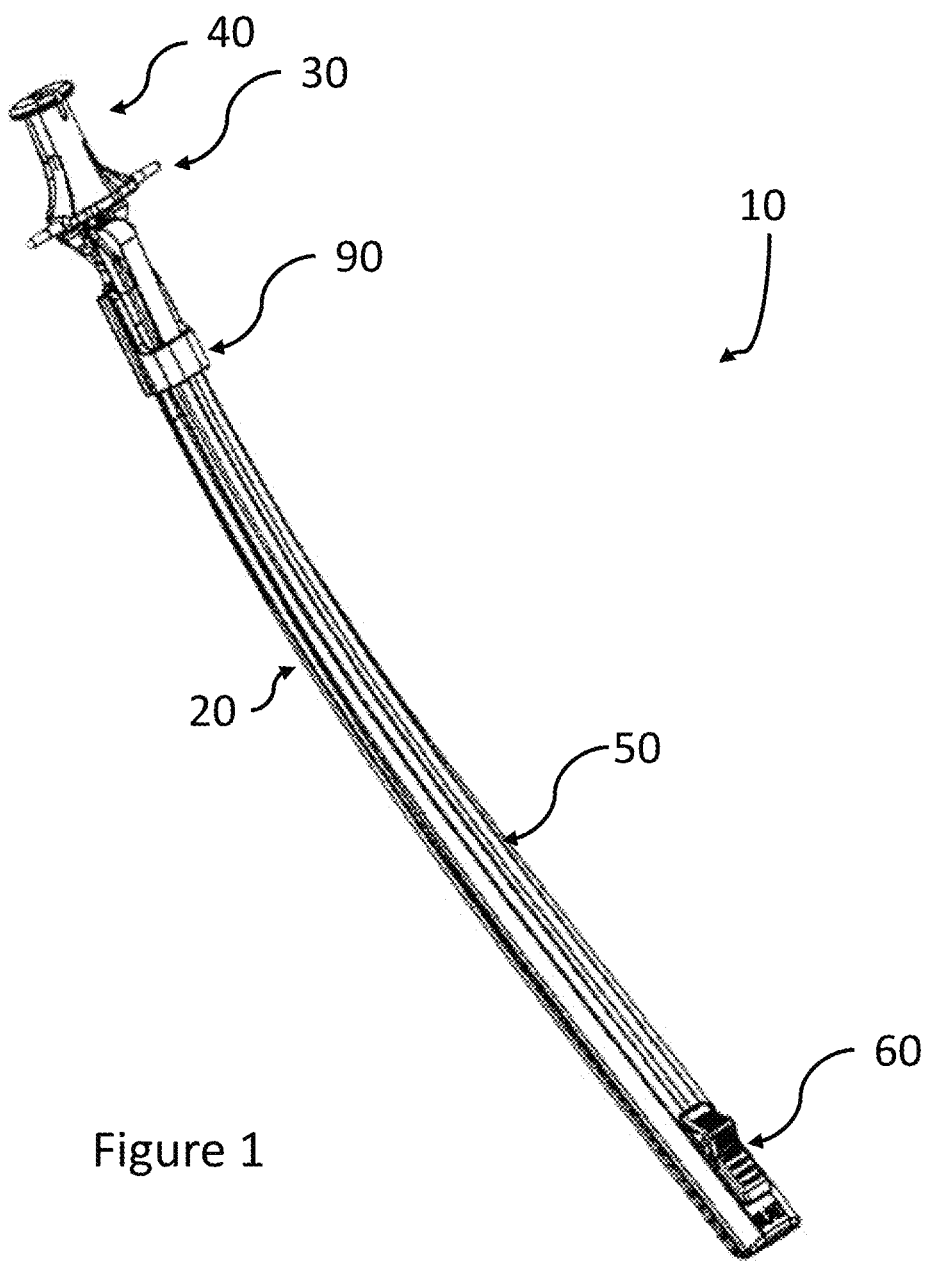
FIG. 1 is a perspective view of an instrument as per present invention.
Figure 2:
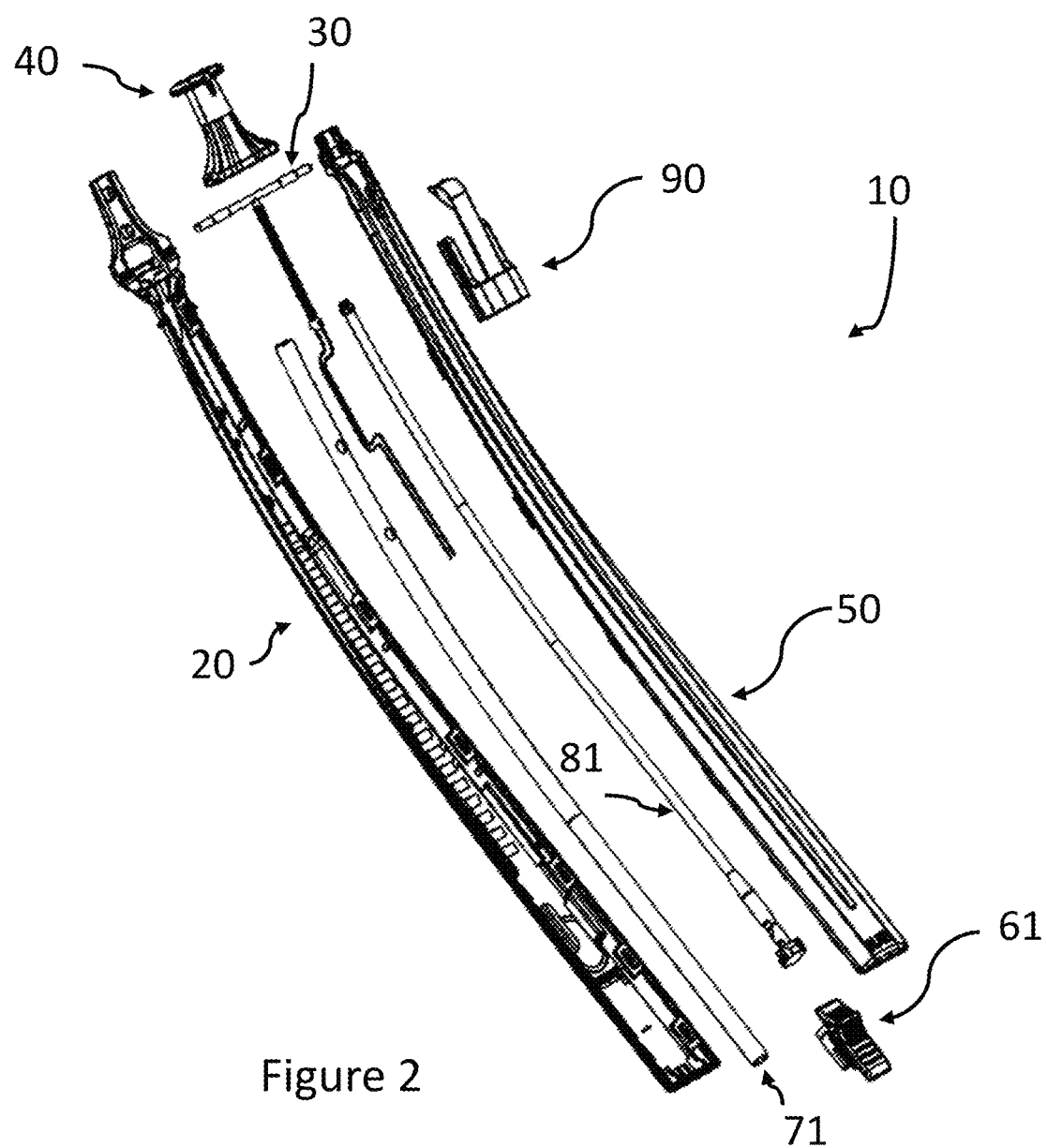
FIG. 2 is an exploded view of the instrument.

FIG. 1, 2 the instrument (10) according to present invention comprises a down foldable "T" shaped intra-uterine device (IUD) (30), a base (20), a navigator (50) an open converger (40), a driver assembly (60), a gated support (90).

Figure 3:
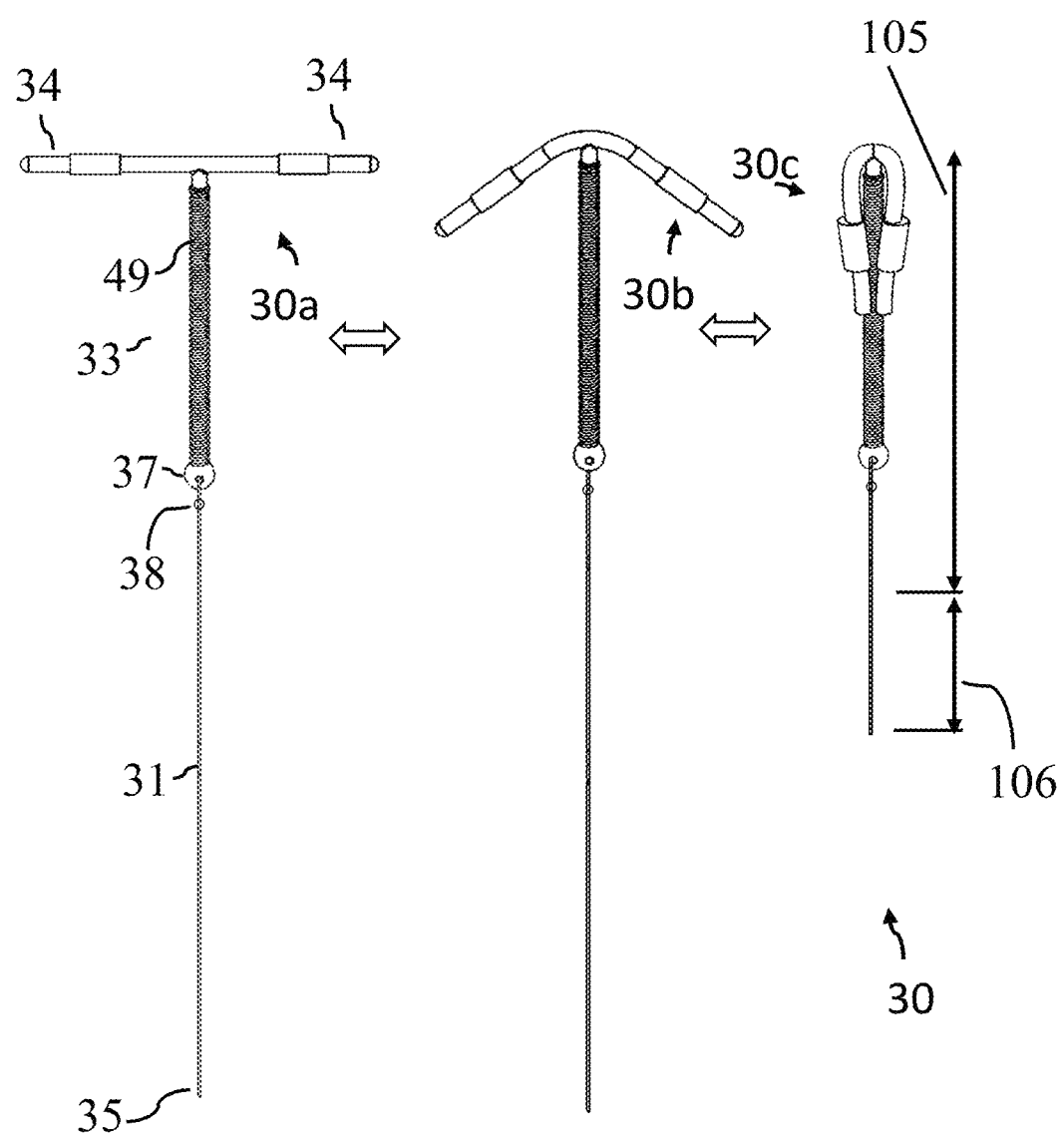
Figure 4A:
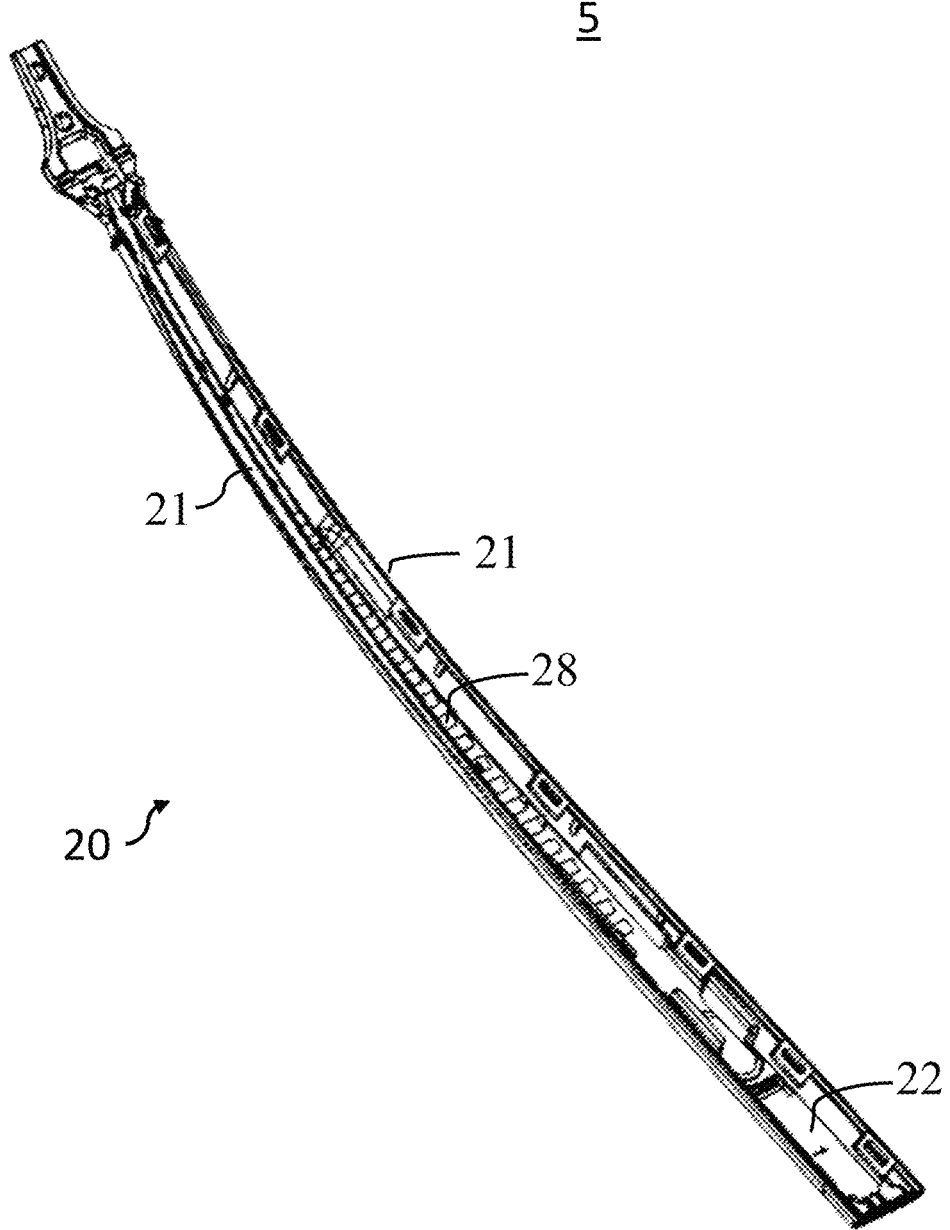
FIG. 4A-4E shows details of a base of the instrument.
Figure 4B:
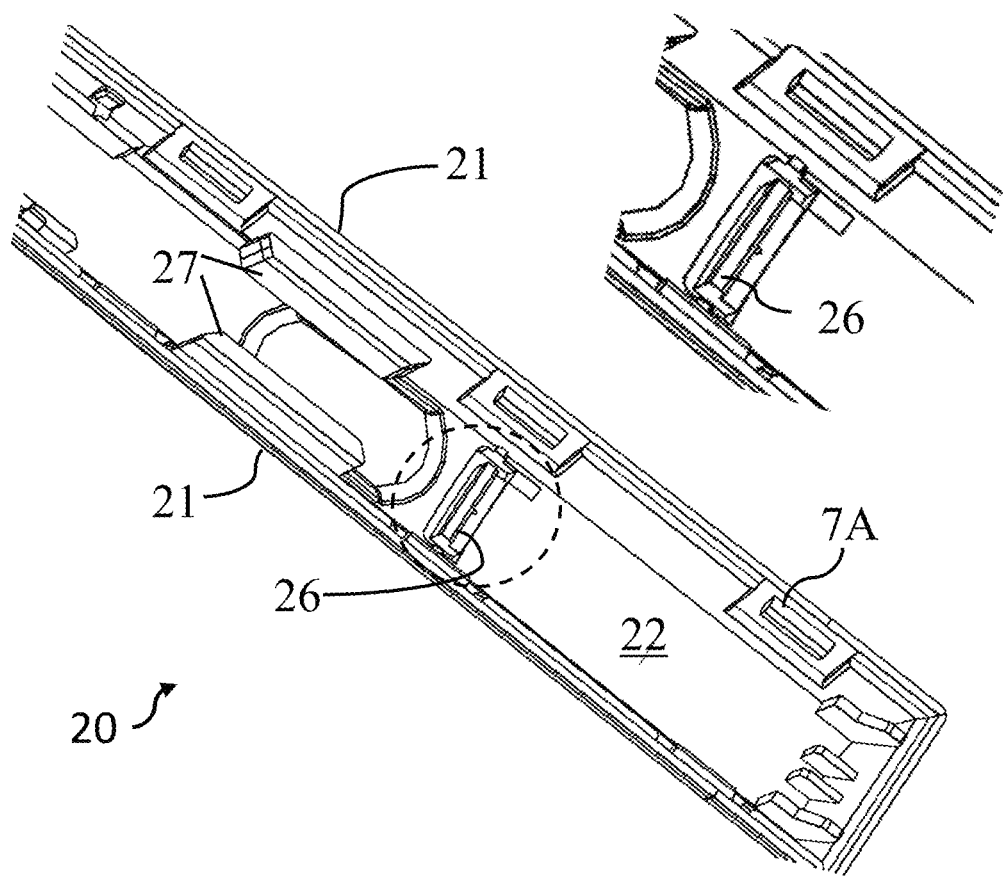
Figure 4C:
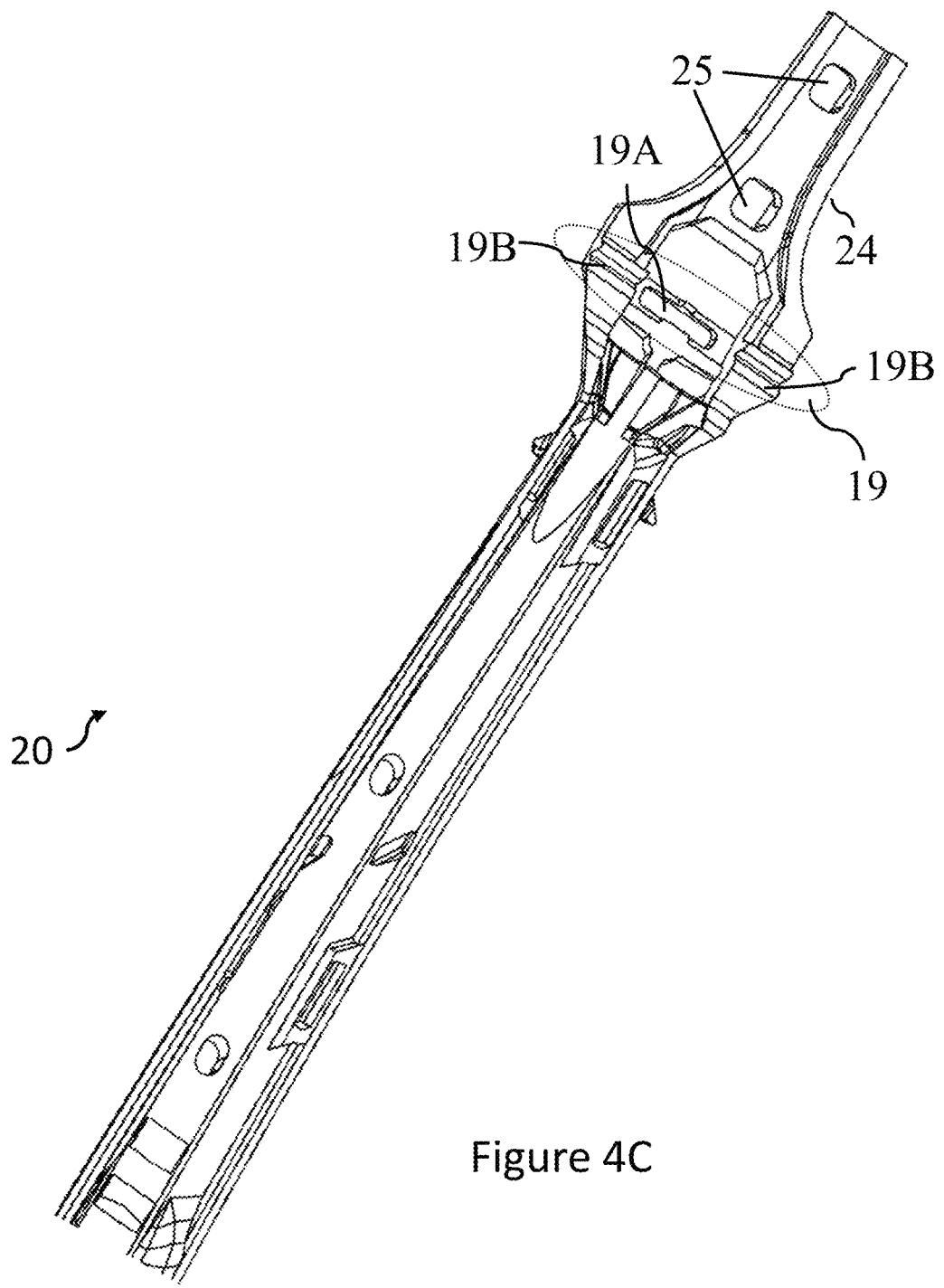
Figure 4D:
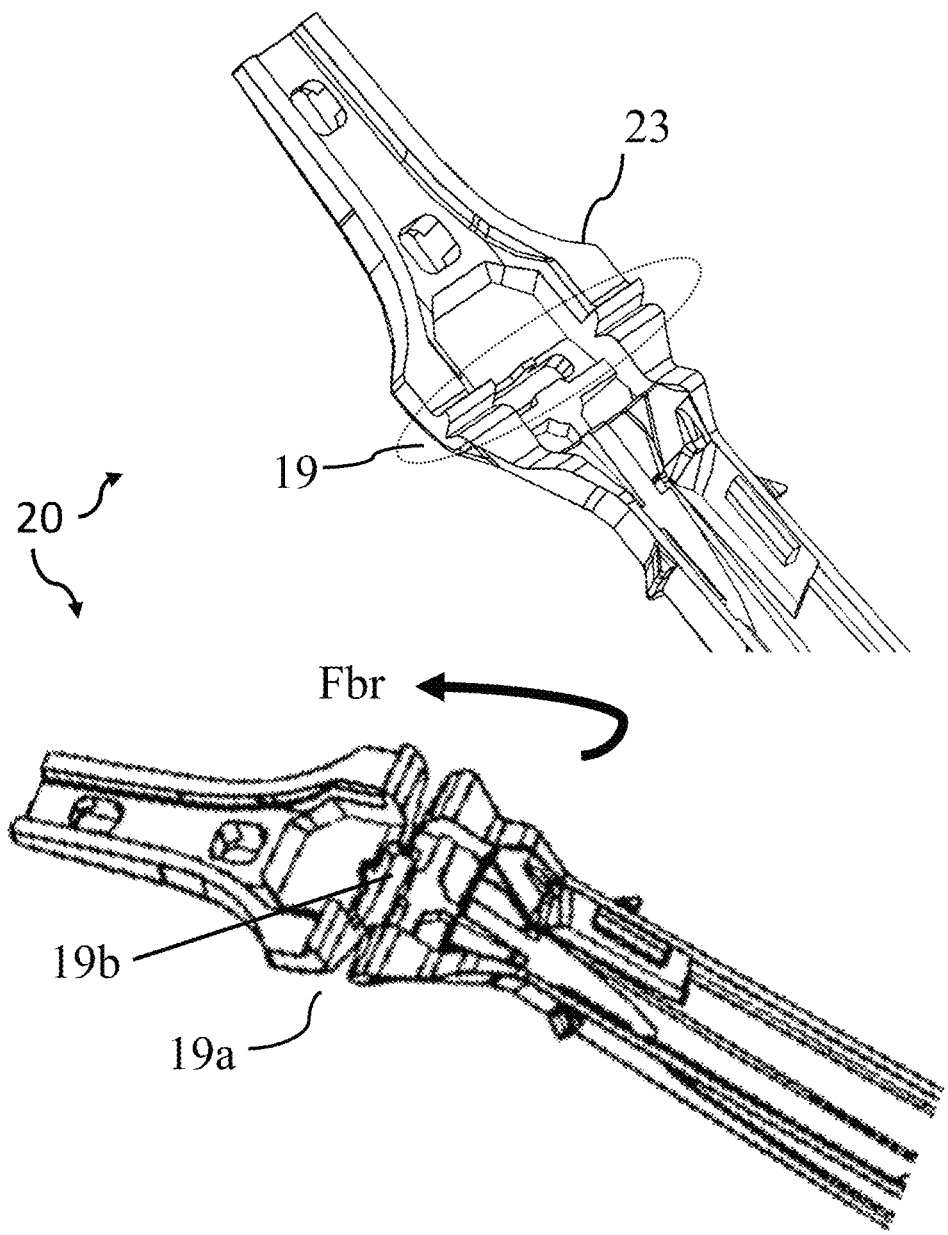
Figure 4E:
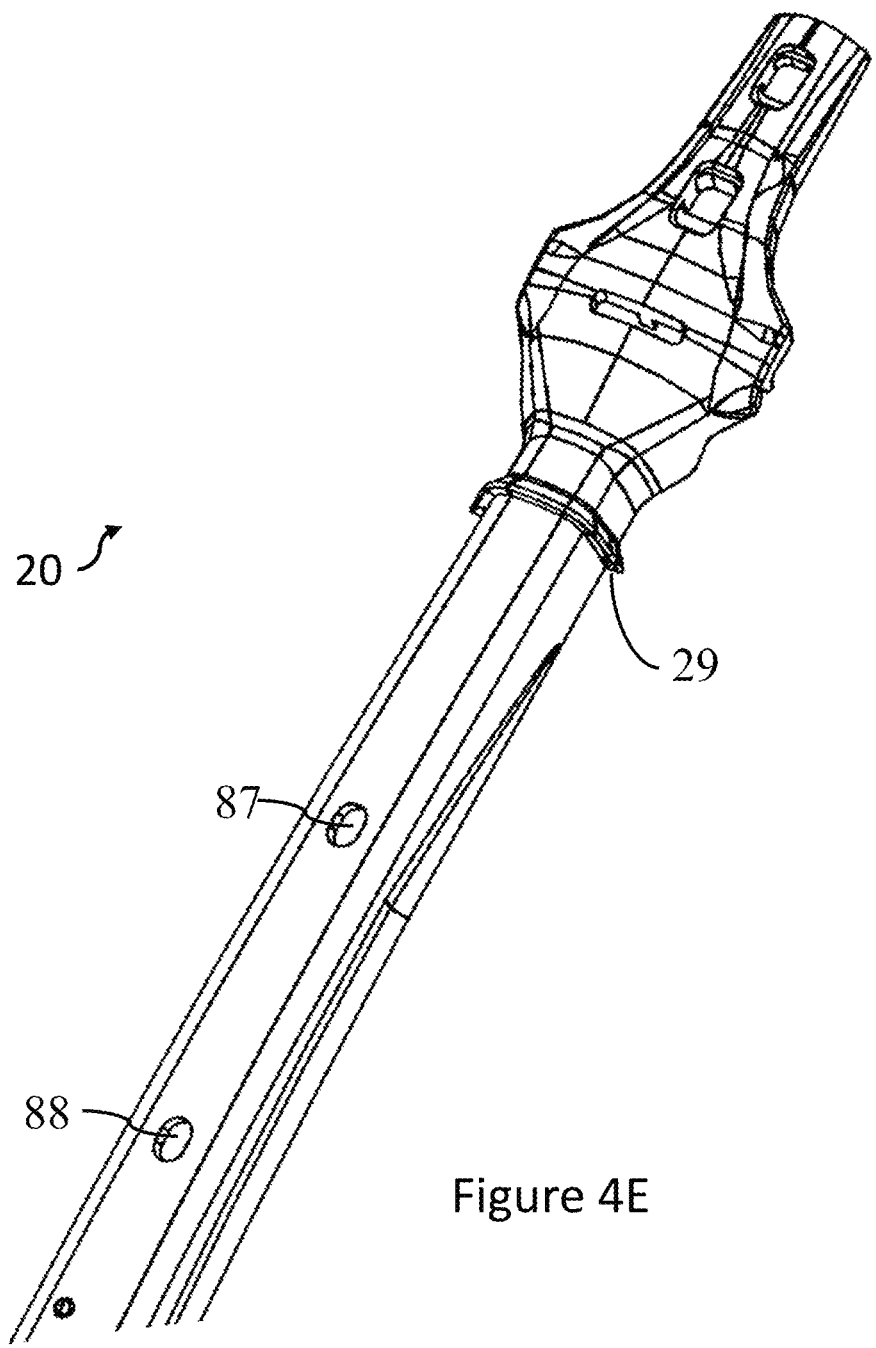

FIG. 3, the preferred embodiment is around the IUD (30) generally comprising a frame having two identical arms (34) on either side of a stem (33), with both arms (34) of the IUD (30) foldable towards the stem (33) of the IUD (30), as shown in FIG. 3. The instrument (10) is shipped when the IUD (30) is with its arms (34) in a "T" formation (30a) with respect to the stem (33), as it should be when placed in uterus of woman. The arms (34) are in a shrunk formation (30c) while inserting in uterus, and in an interim downwards formation (30b) in the course of preparation for insertion. The IUD (30) further comprises a contraceptive material (49) disposed around the stem (33), and at least one string (31) emerges from a lower end (37) of the stem (33), generally via a knot (38). The string (31) has a terminating ends (35). The terminating ends (35) of the string (31) are concealed in the instrument (10).

As shall be evident, the process of loading, inserting in uterus and safely releasing the IUD (30) is carried out by a single hand operation—carrying the instrument between fingers and thumb, and it is of great benefit to the medical service provider. An IUD end (5) and an operator end (6) signifies direction of the instrument (10) and all parts while describing features, sub-assembly, assembly and method of use.

FIGS. 4A-4E, the base (20) has two walls (21) joined by a floor (22) narrowing towards the IUD end (5), widening again to form a platform (23), and converging to a supporting zone (24) having at least a receptacle (25), till an IUD end (5).

The floor (22) has a raised projection emerging from the floor (22) and termed as a delatcher (26), towards an operator end (6); a plurality of first guide fences (27) and an array of unidirectional gear tooth (28). The walls (21) have a plurality of locking projections (7A) all along an upper edge of both walls (21). An outside of the base (20) has a collar (29) towards the IUD end (5). A weakening combination (19) is provided to ensure single-use of the instrument (10). In the preferred embodiment, the weakening combination (19) comprises a pair of weakening notches (19a) and at least a depleted zone (19b) on the platform (23) of the base (20). A force (Fbr) consciously applyable by a medical service provider breaks the floor (22) from the weakening notches (19a), separating a part of the base (20) carrying the open converger (40), and render the instrument (10) non-reusable irreversibly. This inventive construction is indispensable in today's times of viral and bacterial contamination.

Figure 14:
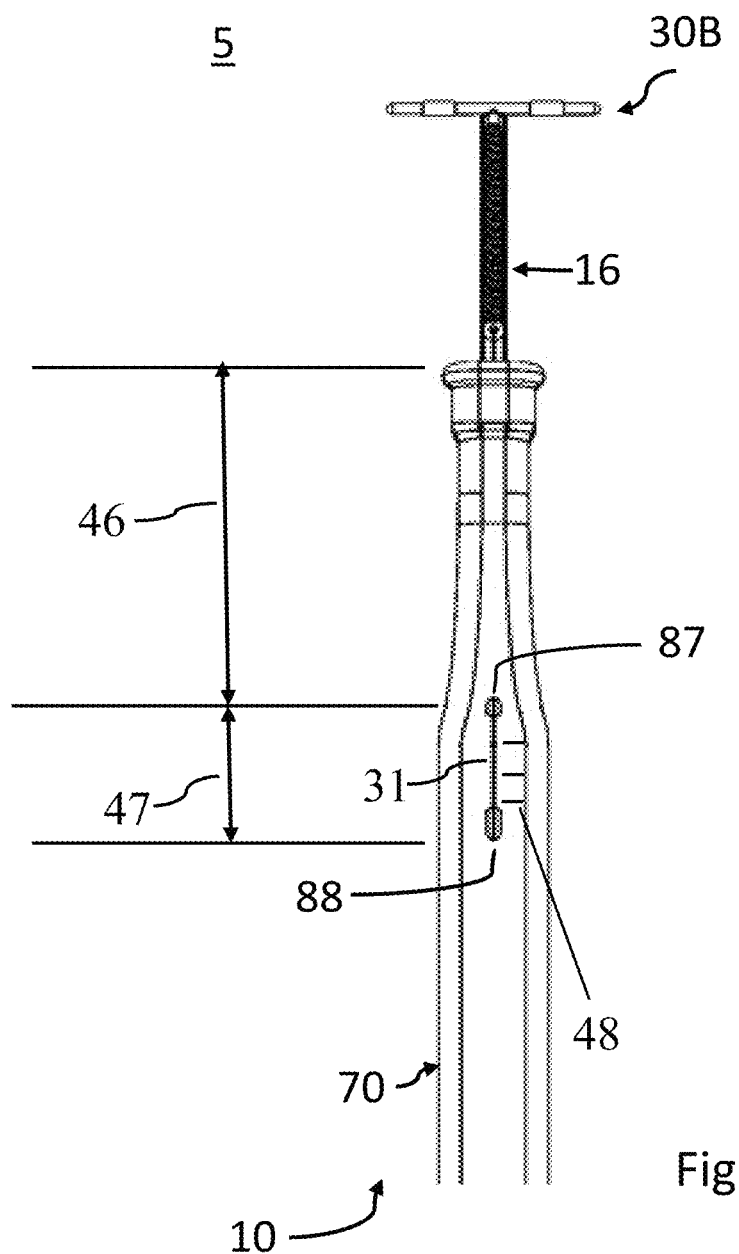
FIG. 14 is a partial front view of a string management arrangement of the instrument.

FIG. 14, 16, there is provided a string management arrangement (80) involving a graduated tube (71), the strings (31) of the IUD (30) and the base (20). In the preferred embodiment, the string management arrangement (80) is disposed on the floor (22) of the base (20). There is provided at least one outpoint (87) and one inpoint (88) on the floor (22) of the base (20). The outpoint (87) and the inpoint (88) is essentially a tapered hole. The string (31) exits from the outpoint (87) and re-enters from the inpoint (88). The string (31) is accessible to the medical service provider between the outpoint (87) and the inpoint (88) and the medical service provider has a preferred option to trim the string (31) as per sounding measurement of uterus of woman, BEFORE inserting the graduated tube (71) in the cervix thereby avoiding use of scissors or cutting tool inside vaginal cavity, and this is most desired, safer and therefore preferred way of using the instrument (10) as per the present invention. The outpoint (87) is at a trim length (46) which corresponds to a minimum recommended excess string length expected to be hanging outside cervical os (101) in vaginal cavity of woman. The inpoint (88) is at a conservative length (47). Medical service provider has the freedom to trim the string (31) anywhere within the conservative length (47). A scale (48) is provided alongside to facilitate precision in trimming.

Figure 5A:
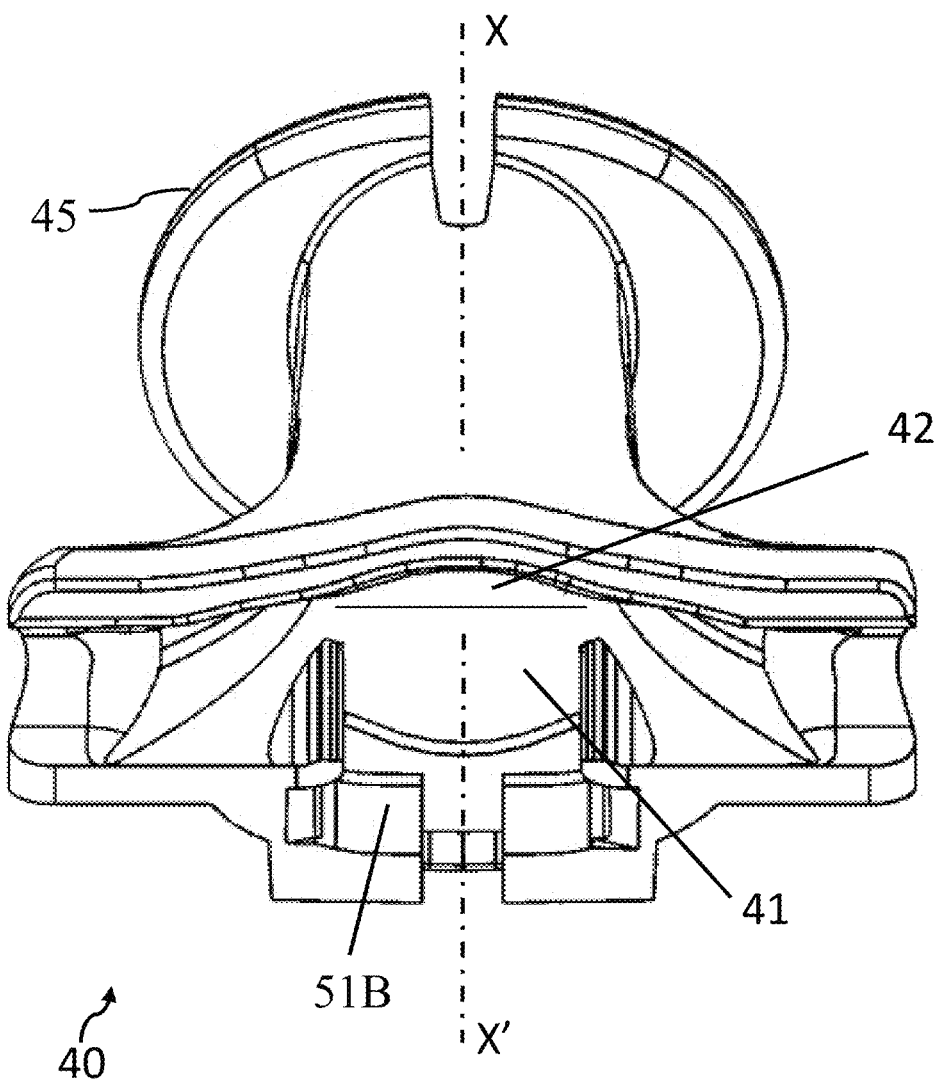
FIG. 5A-5C shows details of an open converger of the instrument.
Figure 5B:
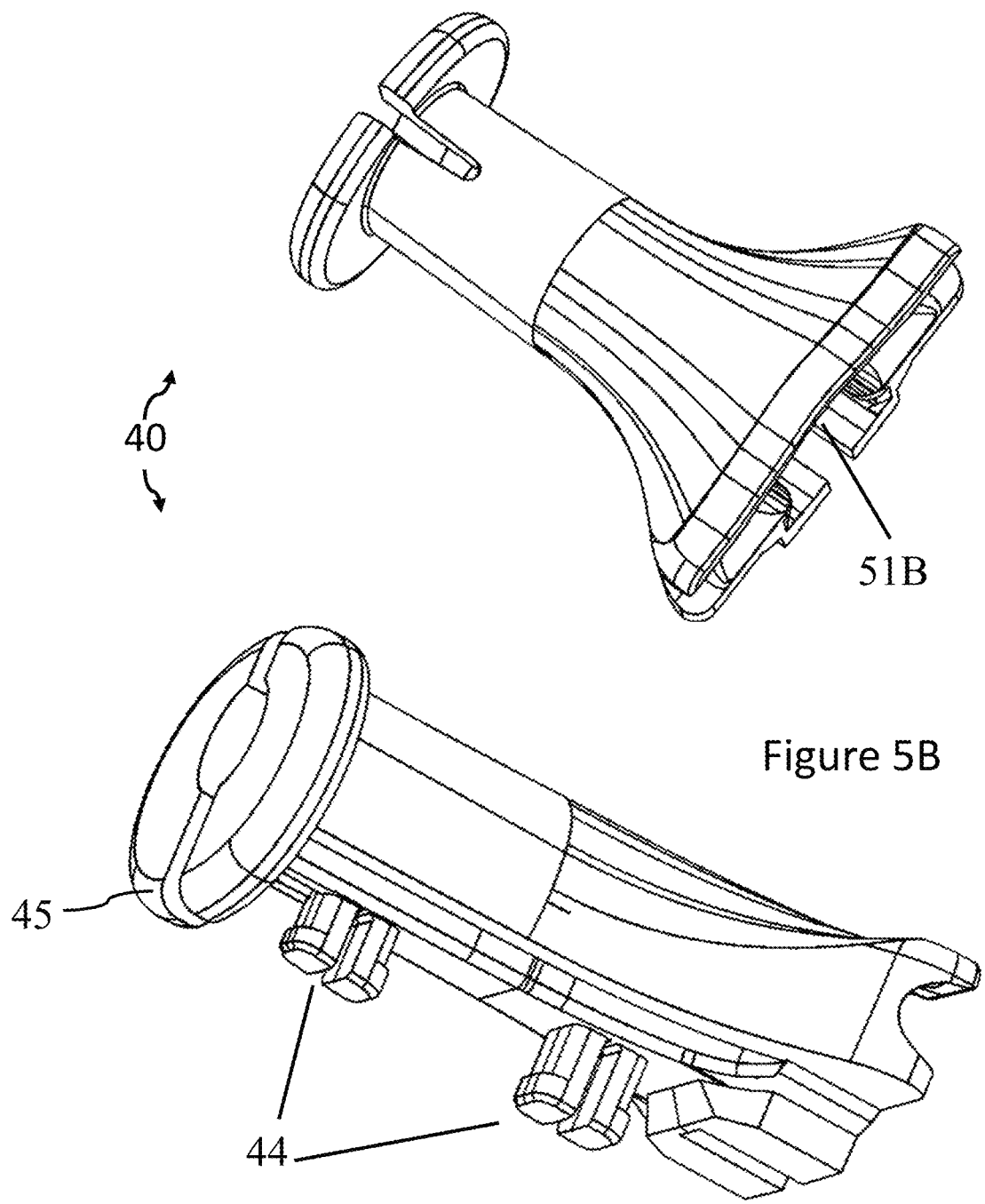
Figure 5C:
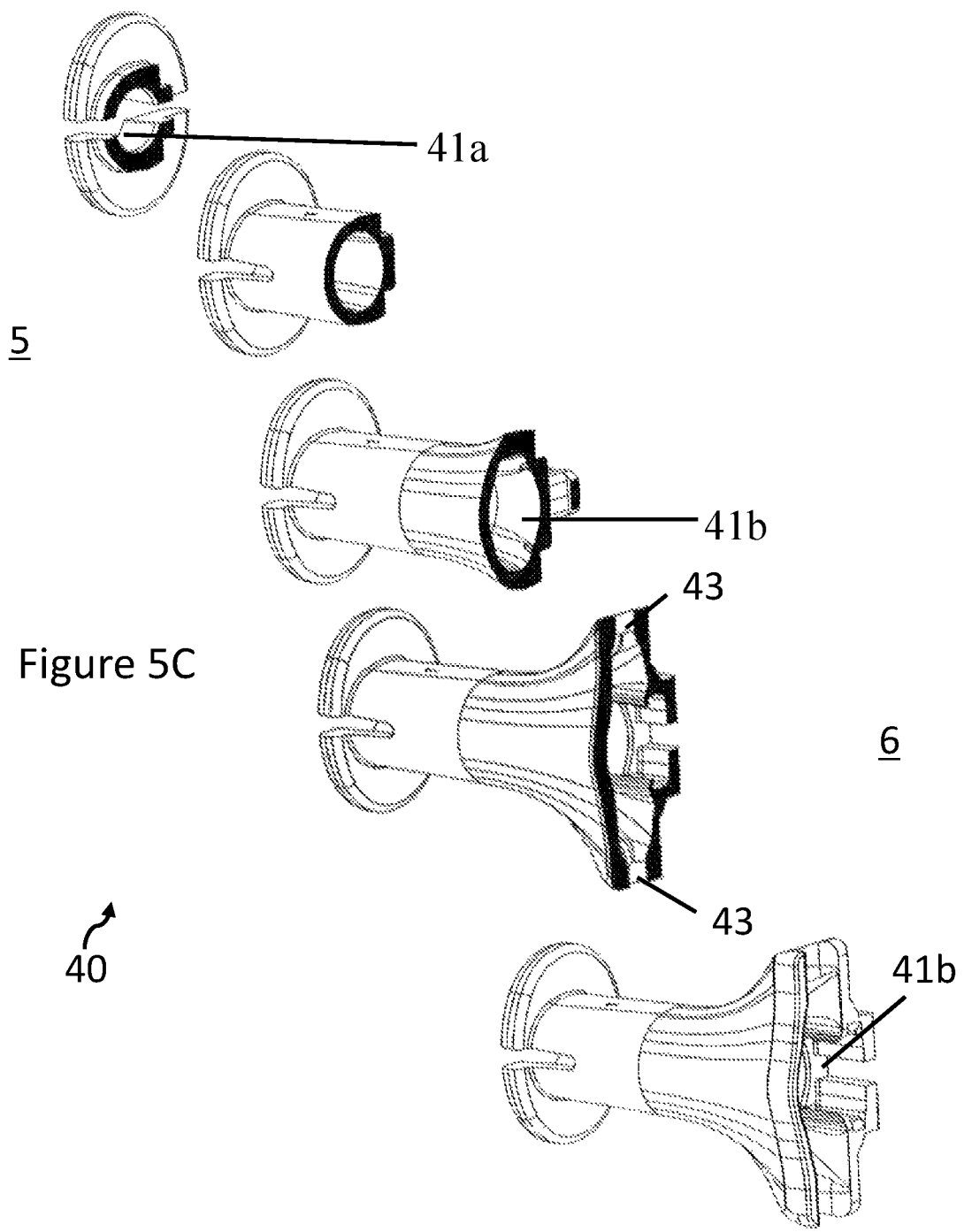

FIGS. 5A-5C, the open converger (40) has a flange (45) towards the IUD end (5), a covered channel (41) commencing with a circular opening (41a), and transitioning gradually to a funneling opening (41b) towards the operator end (6), the covered channel (41) being symmetrical about an imaginary plane passing through a line X-X' and orthogonal to this paper. The covered channel (41) has an additional room (42) towards an upper side. The funneling opening (41b) diverges to two dome shaped openings (43) on either side of the open converger (40). The open converger (40) has reversibly collapsible projections pair (44) corresponding to the receptacles (25) in the supporting zone (24) of the floor (22) of the base (20). There is provided an alignment socket (51B) on a lower side. The open converger (40) is preferably made of a tough, transparent and virgin engineering thermoplastic, so the medical service provider has a comfort to visually ensuring a proper downfolding of the IUD (30).

Figure 6:
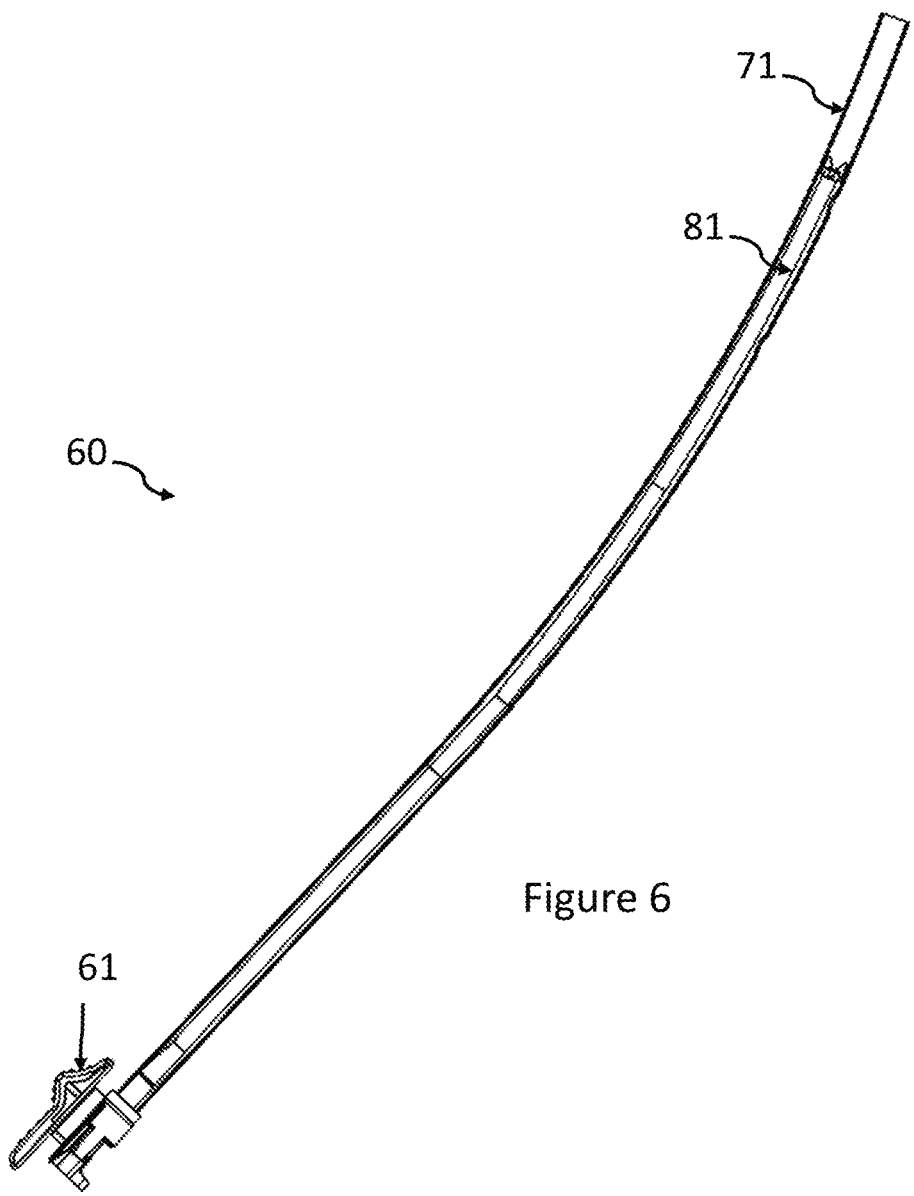
FIG. 6 is a sectional view of a driver assembly of the instrument.

FIG. 6, the driver assembly (60) comprises:
A bidirectional carrier (61)
A graduated tube (71)
A latching rod (81)

Figure 7:
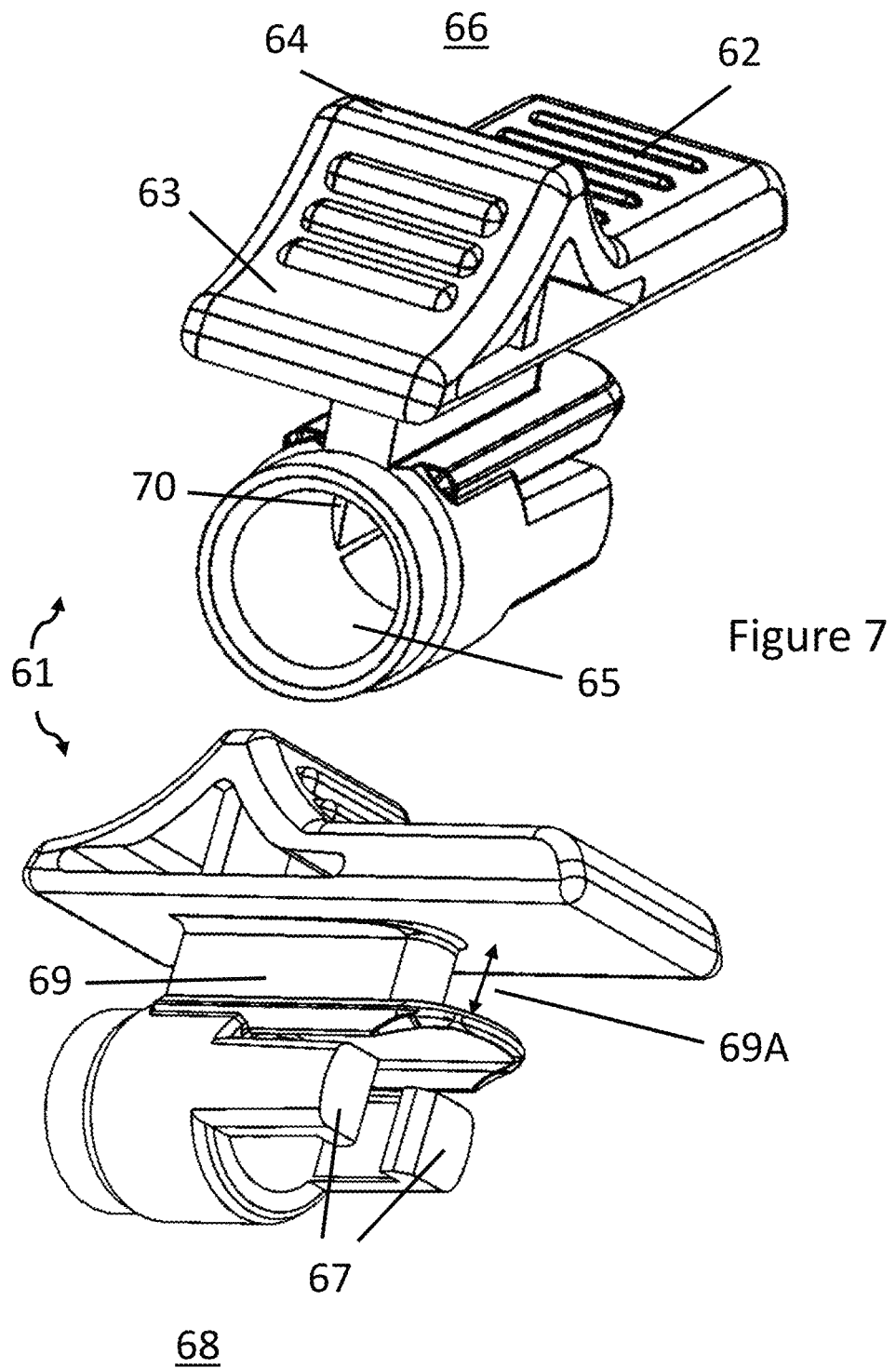
FIG. 7 shows two perspective views of a bidirectional carrier of the driver assembly.

FIG. 7, the bidirectional carrier (61) has a push zone (62) and a pullback zone (63), separated by a cliff (64) on an upper side (66). There is a tube receptacle (65) on a lower side (68) and a pair of locking teeth (67) with a back face (70) integrated to an open end of the tube receptacle (65). The upper side (66) and the lower side (68) are joined by an interfacing wall (69) between a bottom side of the push zone (62)+the pullback zone (63) and an upper side of the tube receptacle (65), forming travel ways (69A) on either side of the interfacing wall (69).

Figure 8:
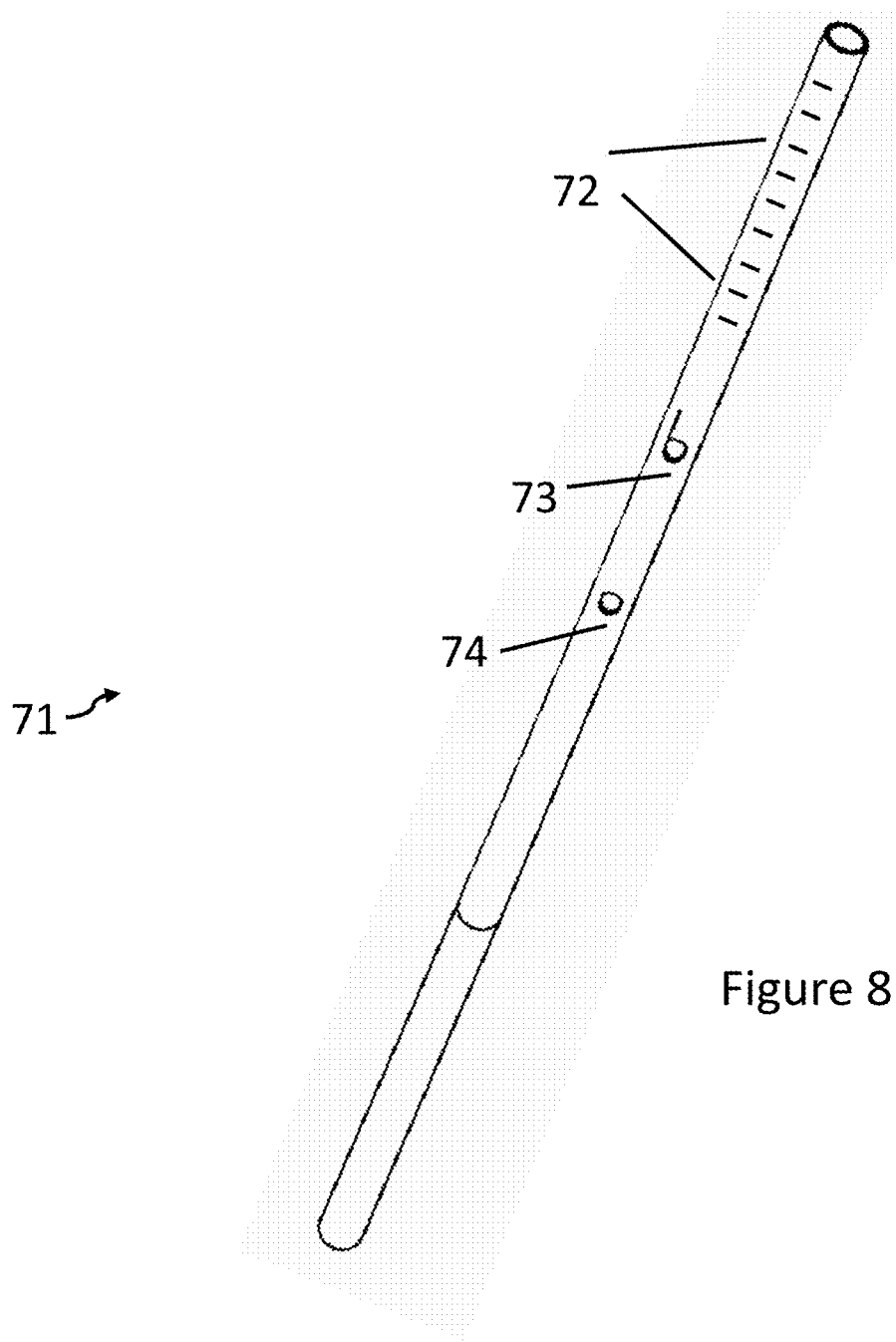
FIG. 8 is a perspective view of the graduated tube of the driver assembly.

FIG. 8, the graduated tube (71) has a plurality of sounding markings (72). There are provided at least an exit hole (73) and optionally an entry hole (74) on an opposite side of the sounding markings (72).

Figure 9A:
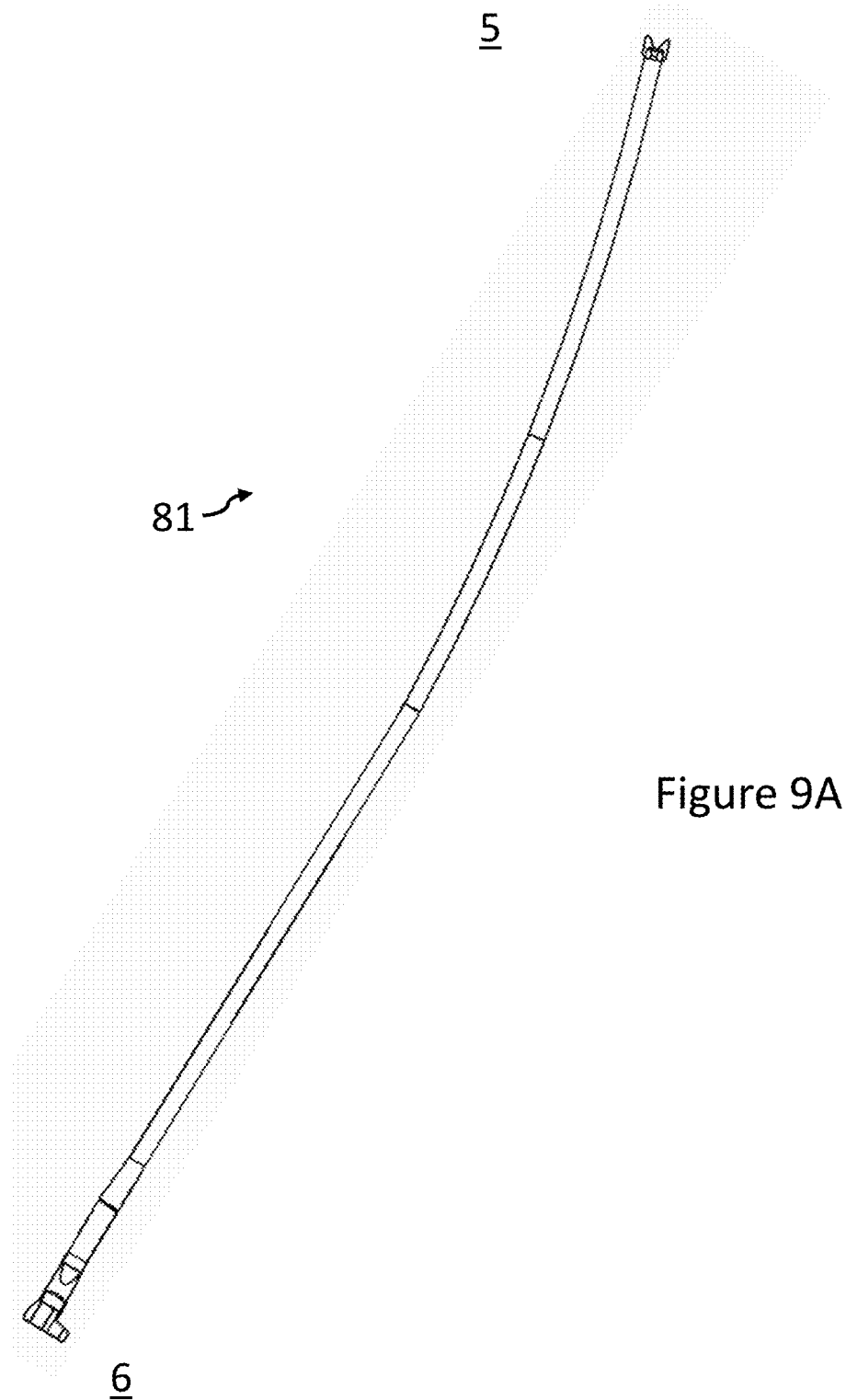
FIG. 9A-9C shows details of a latching rod of the driver assembly.
Figure 9B:
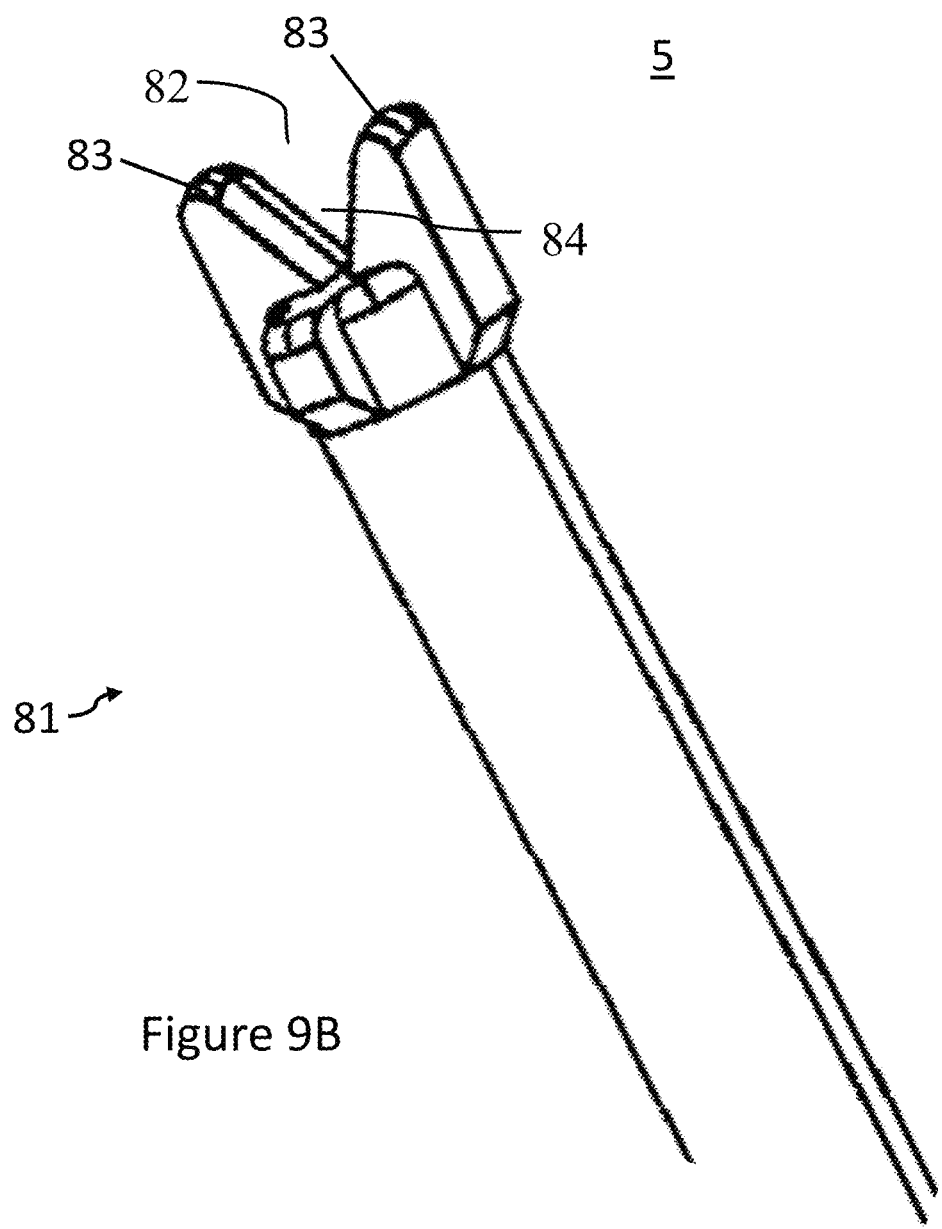
Figure 9C:
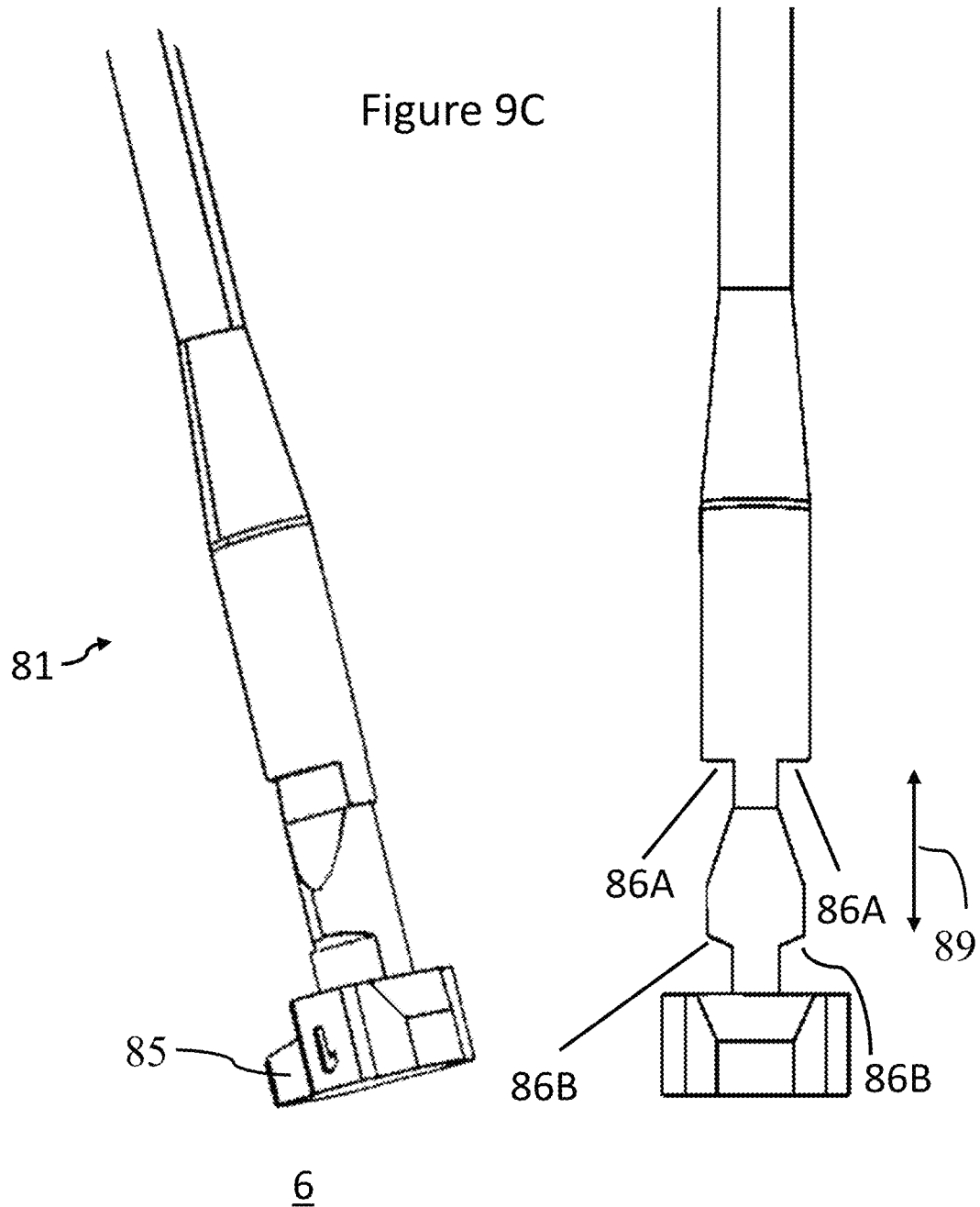

FIGS. 9A-9C, the latching rod (81), has, on the IUD side (5), a conical seat (82) having two resting points (83) and a knot room (84), reserved for the knot (38) of the string (31) of the IUD (30). On the operator side (6) is provided a progressively increasing cylindrical portion, a first pair of seats (86A), again progressively increasing to a second pair of seats (86B), and a downward projection (85). The first pair of seats (86A) is at a measure of length (89) with respect to the second pair of seats (86B)

Figure 11A:
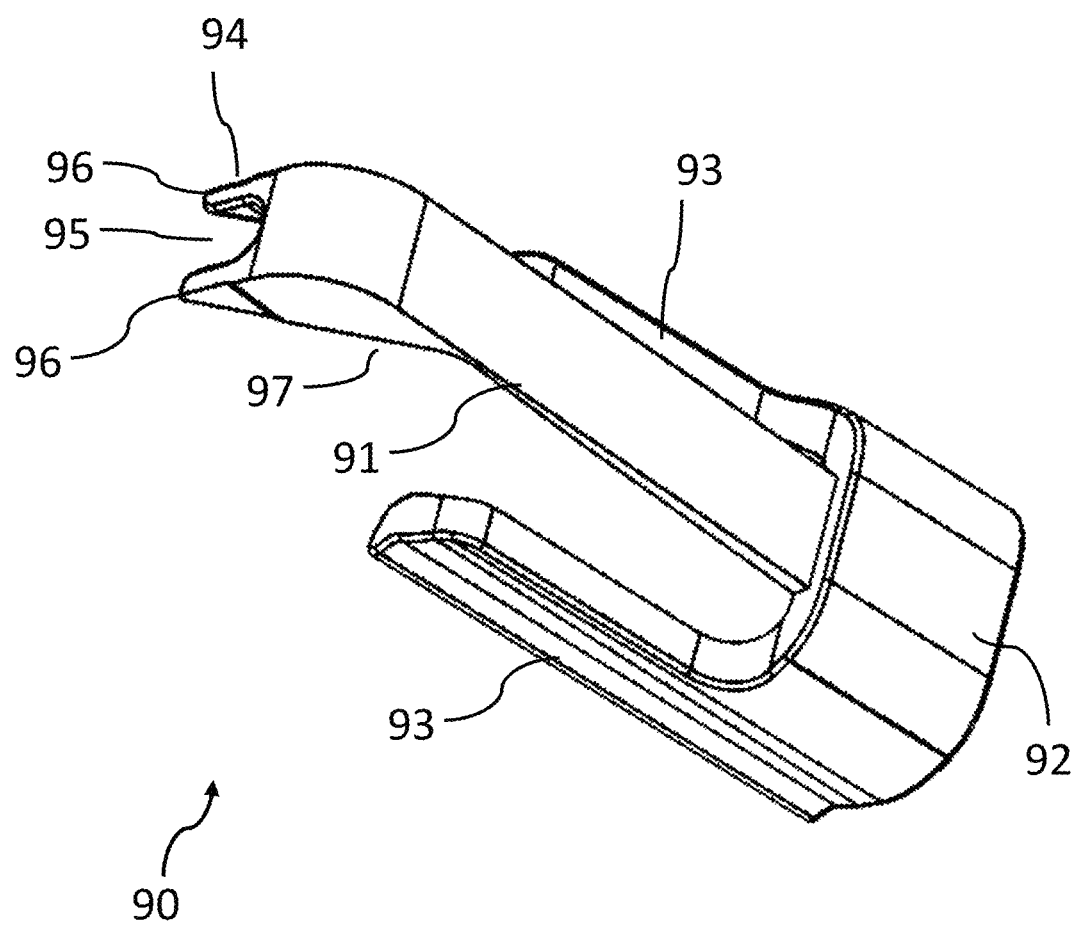
FIG. 11A-11B shows details of a gated support of the instrument.
Figure 11B:
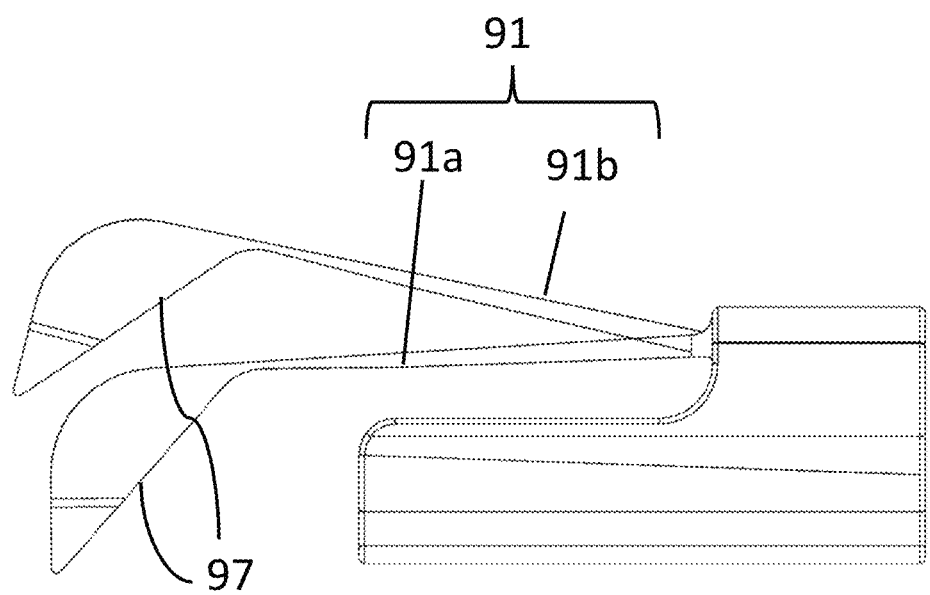
Figure 11B:
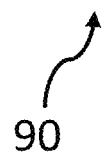

FIG. 11A-11B, the gated support (90) has a leafy arm (91) having a holder (92) at one end, and a downward fork (94) forming an inverted "U" gate (95) having sloped edges (97) with end points (96), at the other end. The holder (92) has an elongated grip (93) on either side. The leafy arm (91) acts as a leaf spring which returnably lifts up between a first position (91a) and a second position (91b).

Figure 10A:
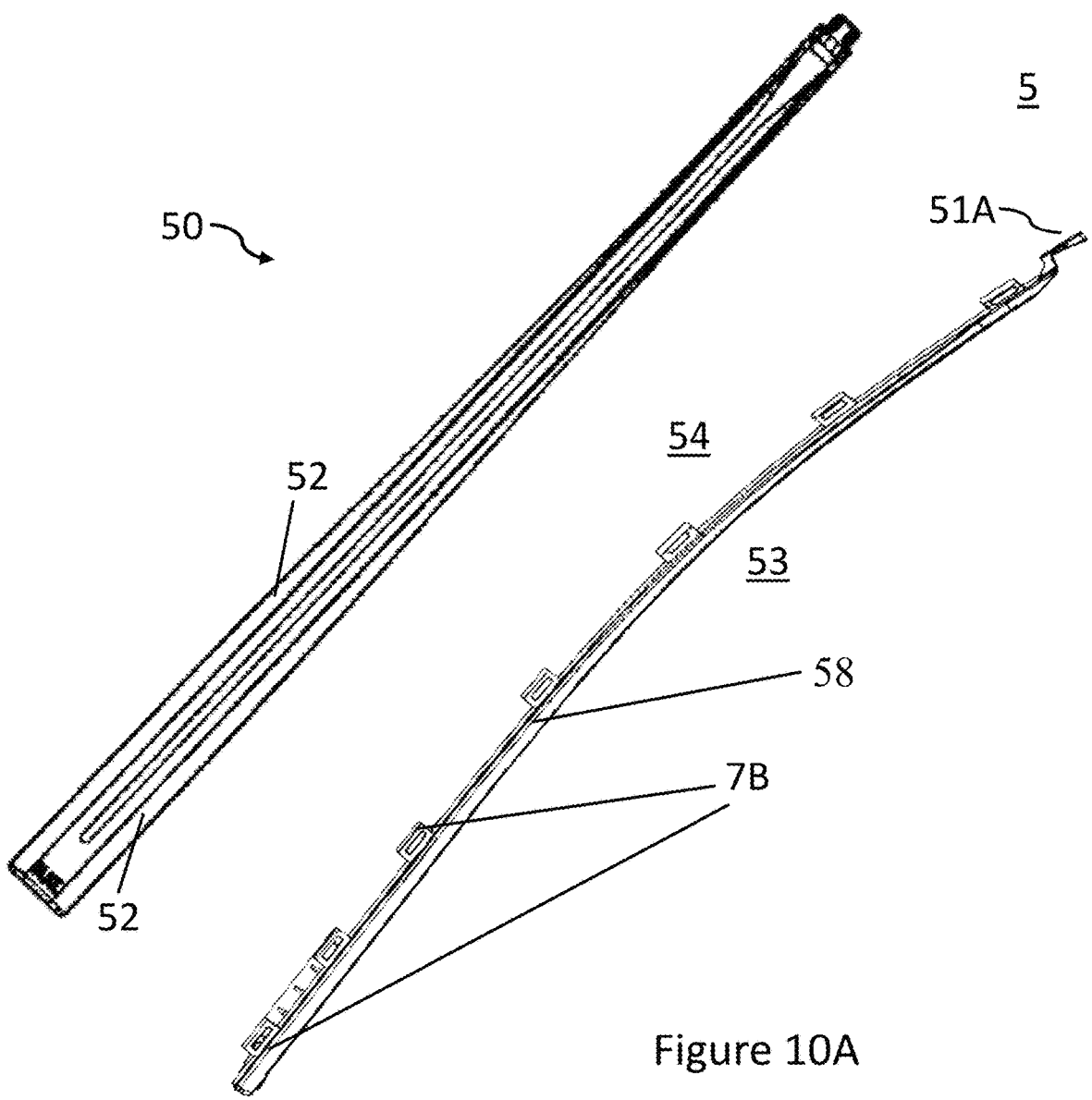
FIG. 10A-10B shows details of a navigator of the instrument.
Figure 10B:
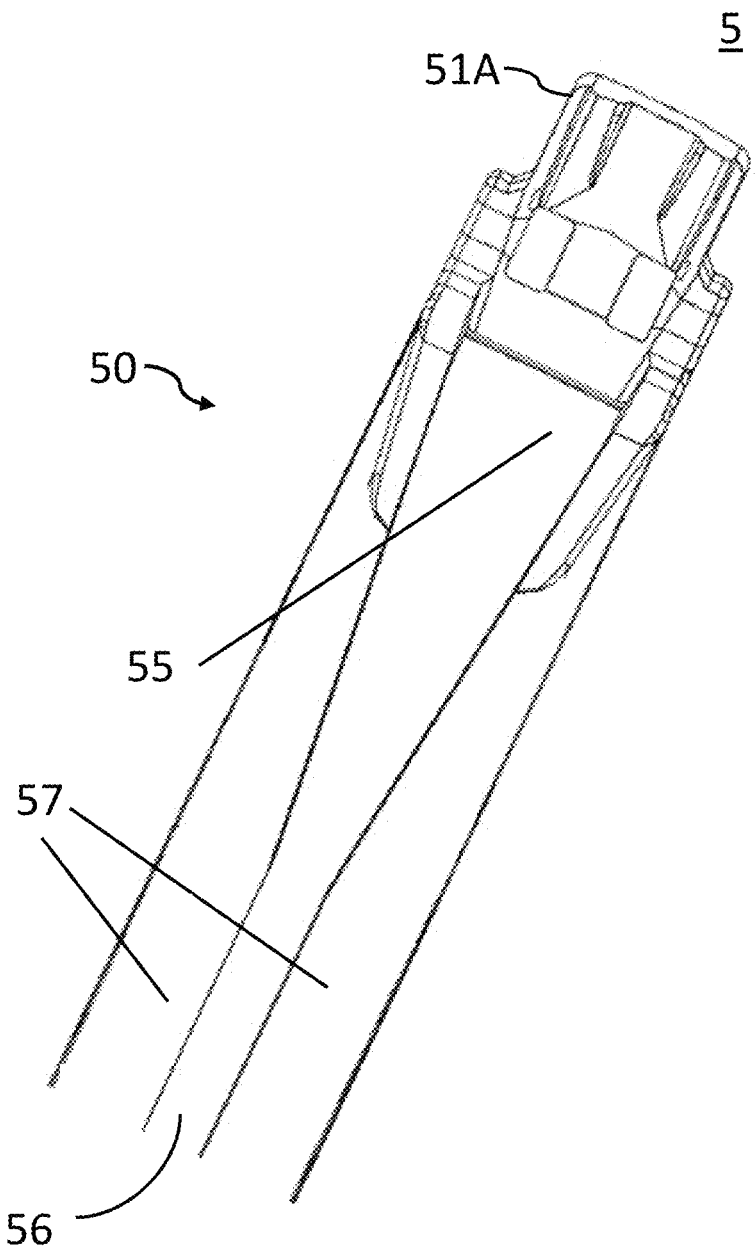
Figure 12A:
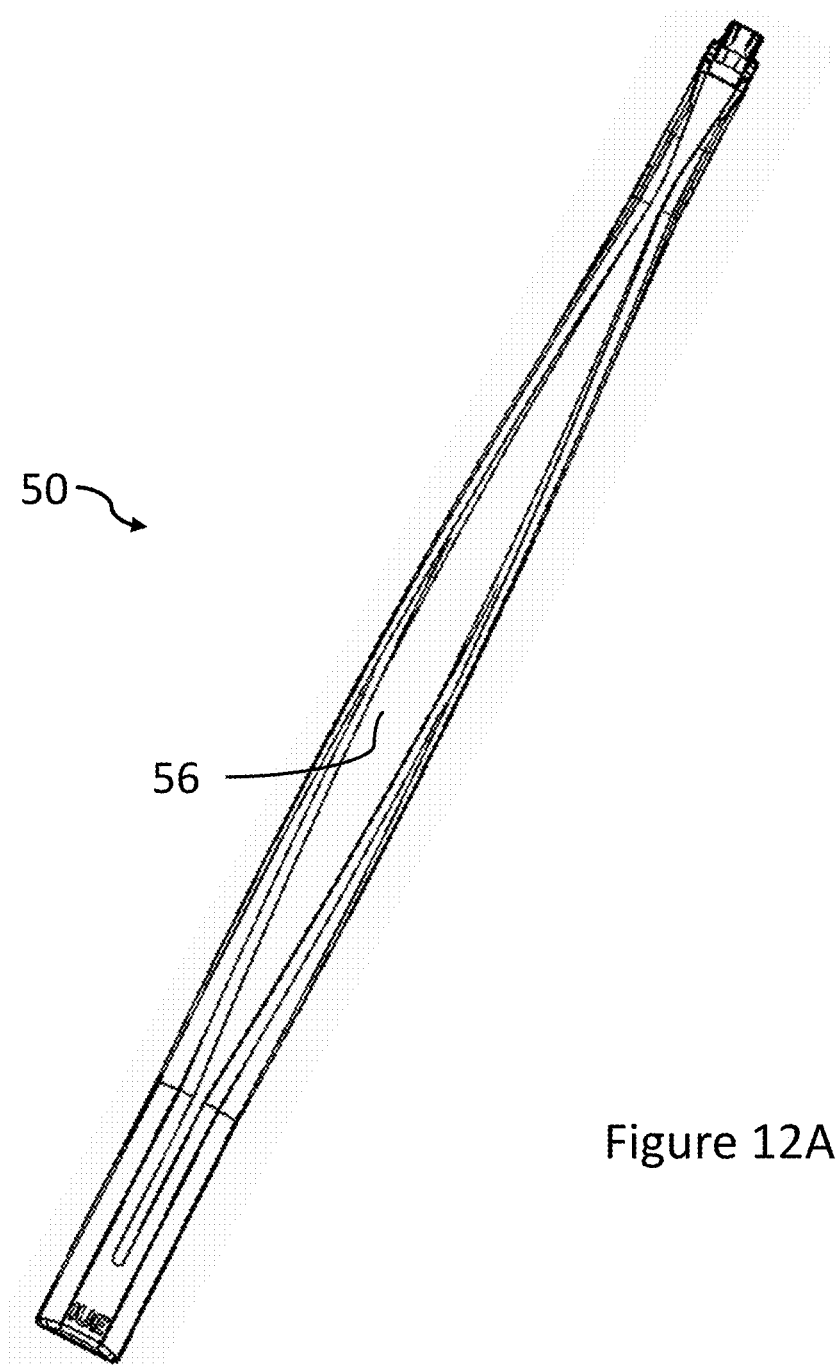
FIG. 12A-12C are constituents of the driver assembly.

FIG. 10A-10B, the navigator (50) has an aligner plug (51A) at its IUD end (5), two mirror symmetrical fences (52) along an entire length of the navigator (50), joining together at the operator end (6), thereby forming a slot (56) with a divergence (55) towards the IUD end (5). The fences (52) have a user side (53) and a concealed side (54). The user side has a flat runway (57) on either side of the slot (56). The concealed side (54) has a guide wall (58) on either side of the slot (56) and a plurality of complementary lockable windows (7B) all along an external edge of both mirror symmetrical fences (52). Consequent to a slender shape of the navigator (50), the slot (56) can be widened temporarily, FIG. 12A.

Figure 12B:
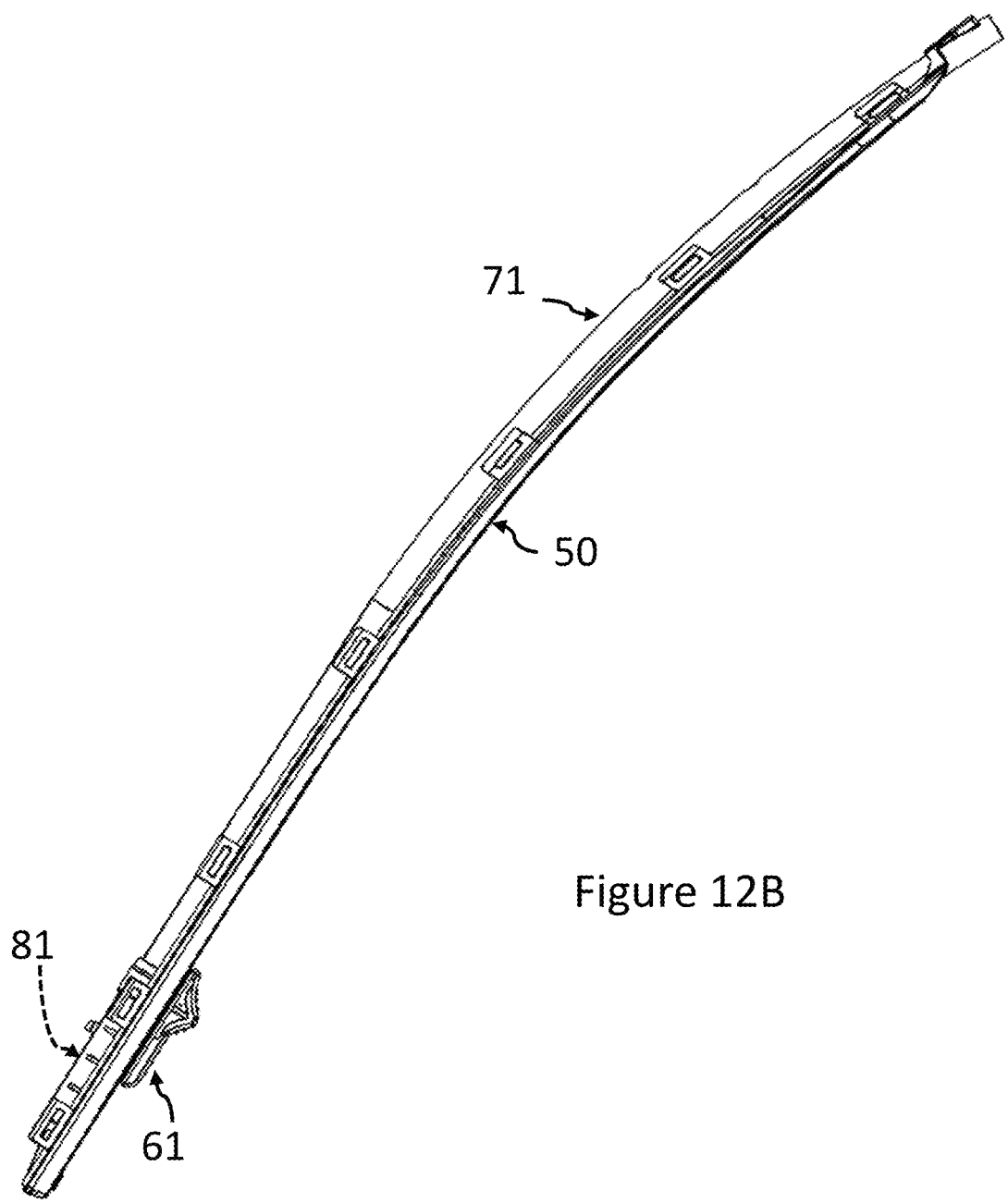
Figure 12C:
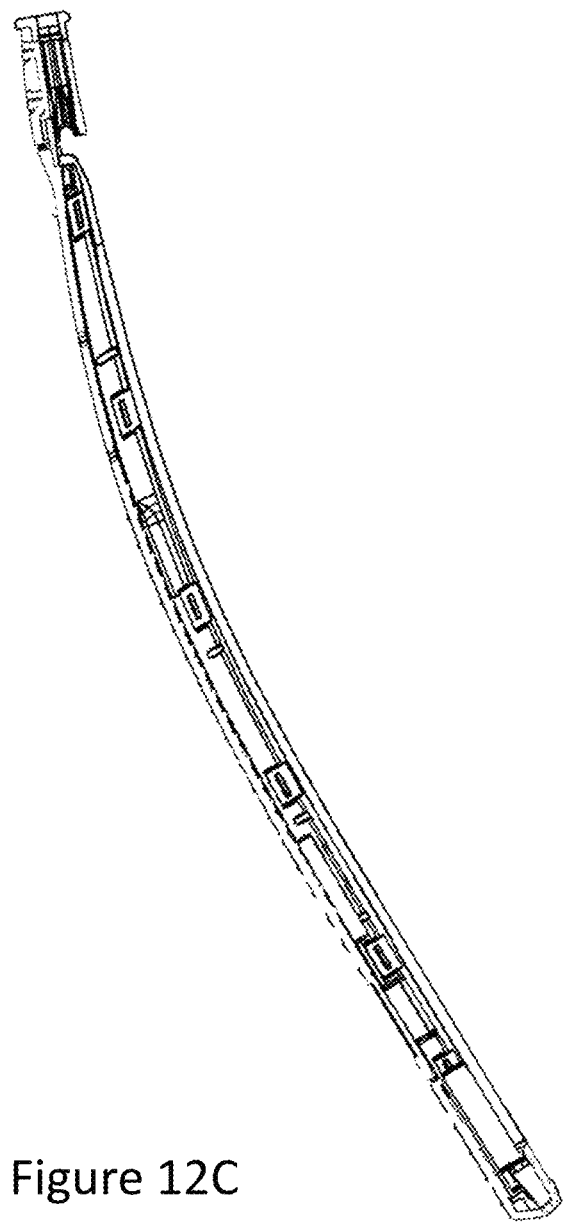
Figure 15A:
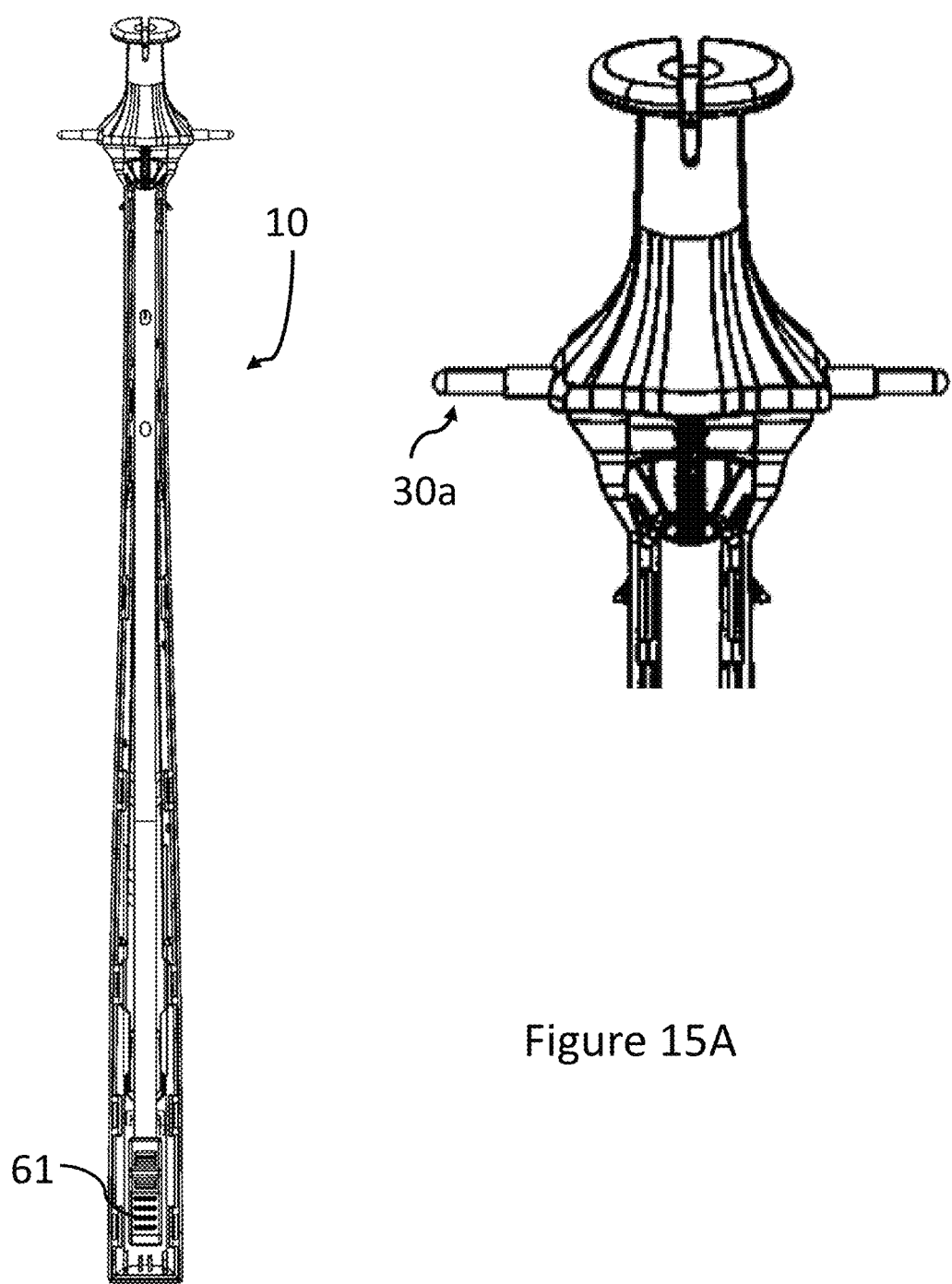
FIGS. 15A, 15B, 15C, 15D, 15E, 15F, 15G, 15H, 15J, 15K, 15L are frontal views of various stages of downfolding and safely placing the IUD.
Figure 15B:
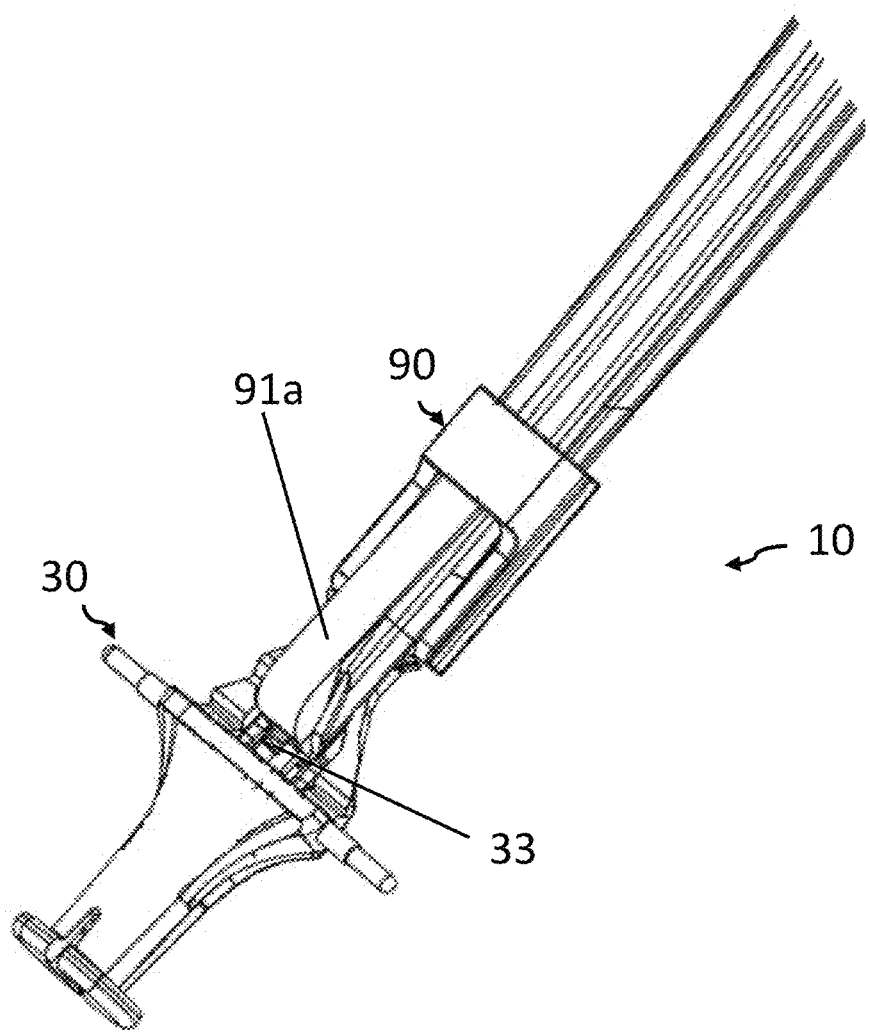
Figure 15C:
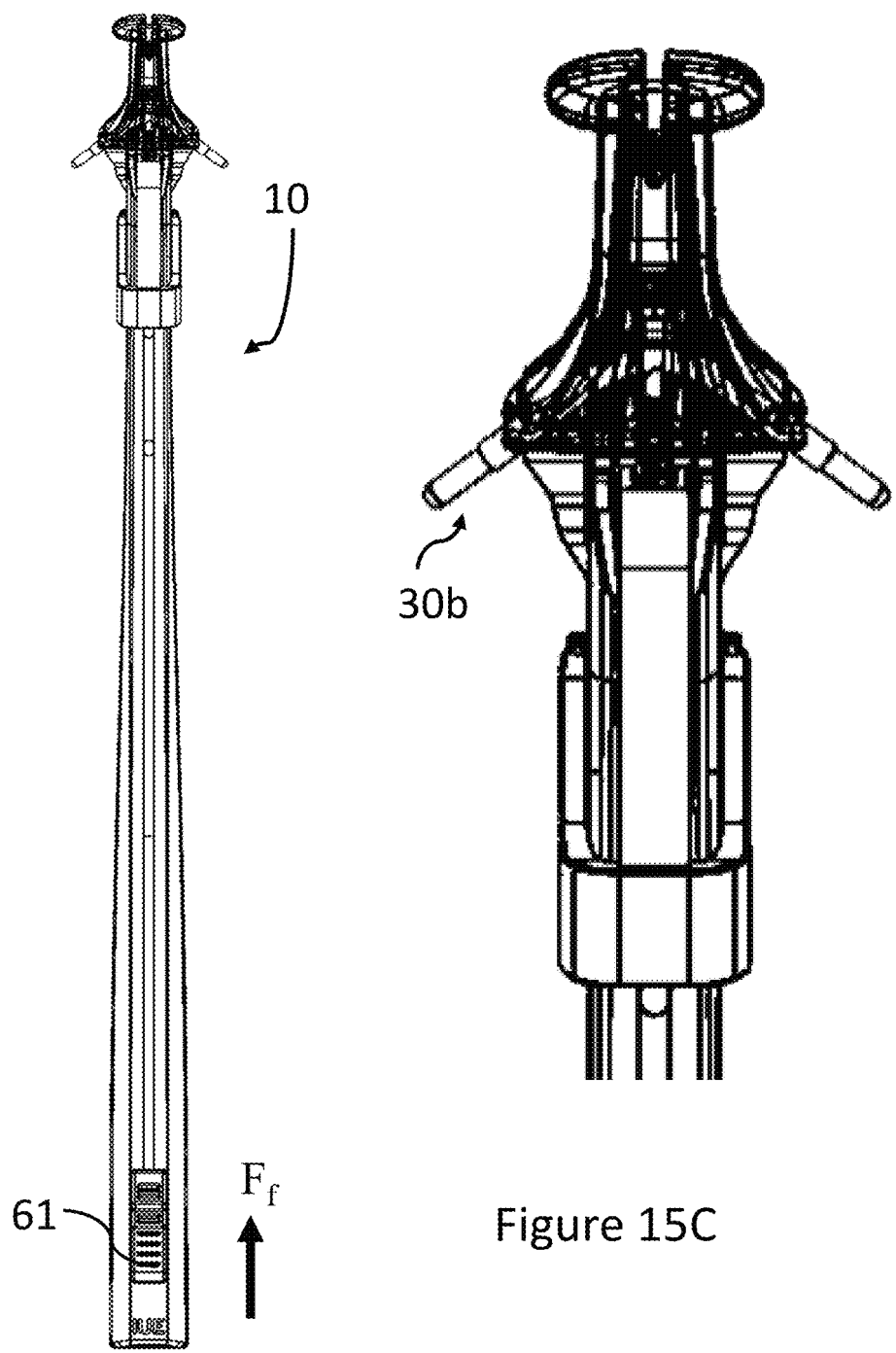
Figure 15D:
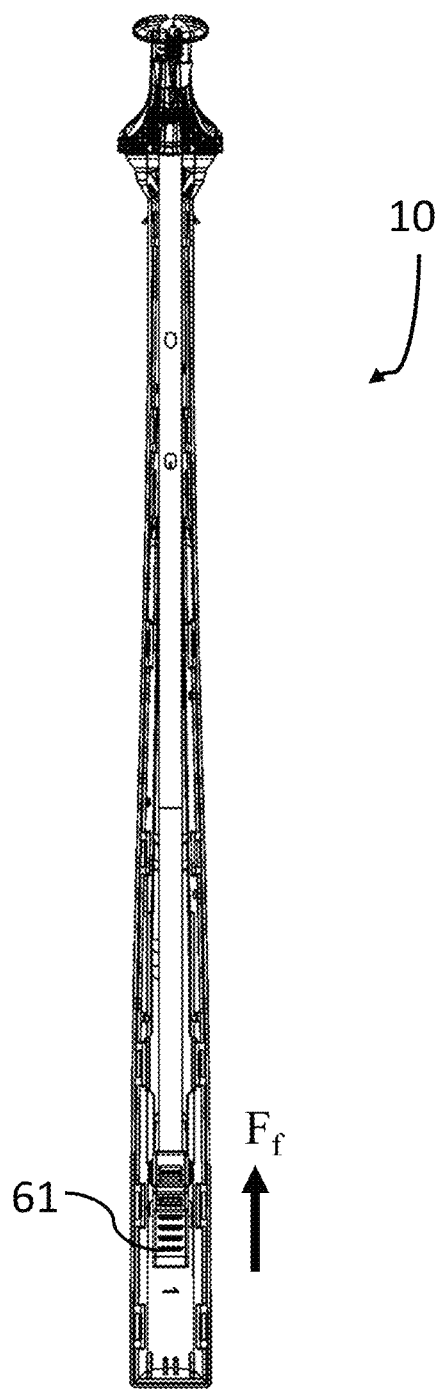
Figure 15E:
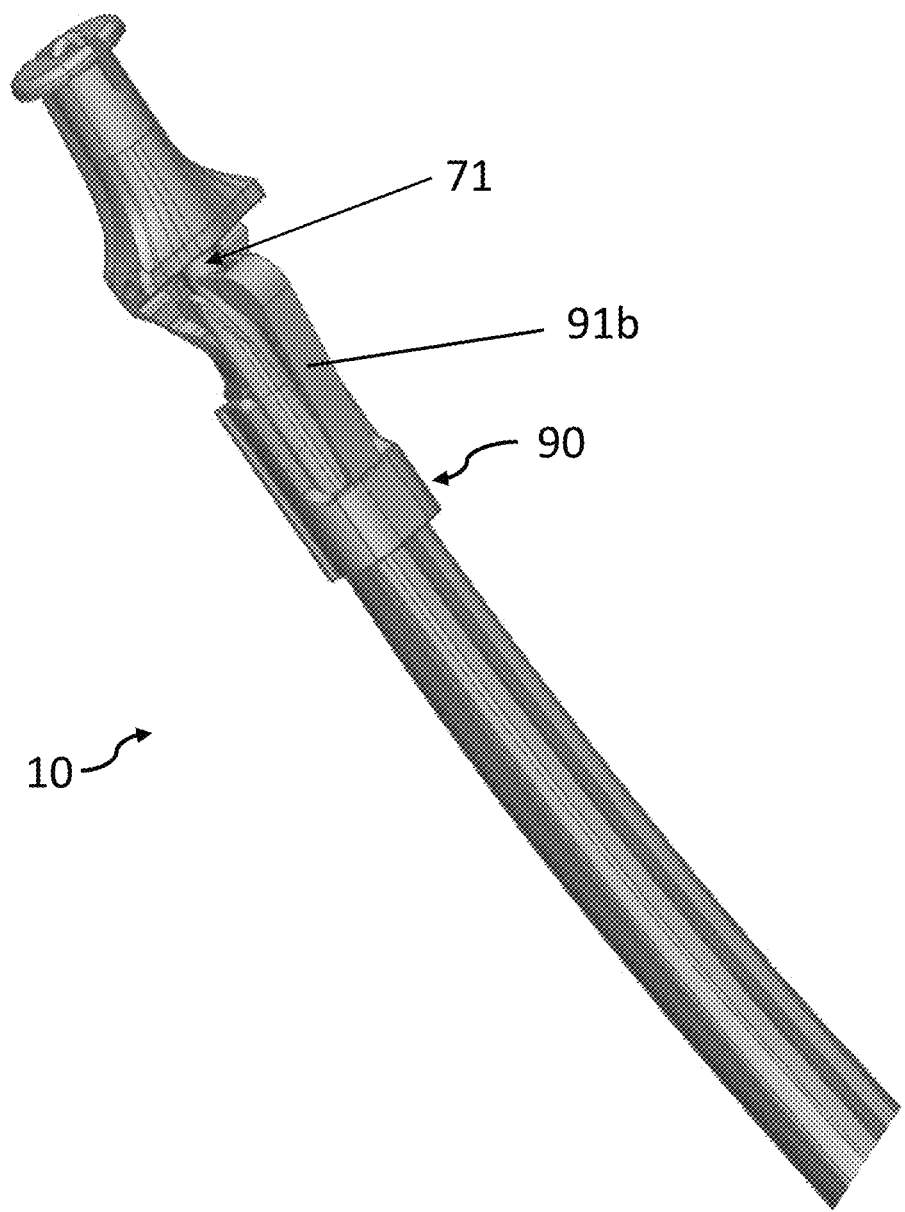
Figure 15F:
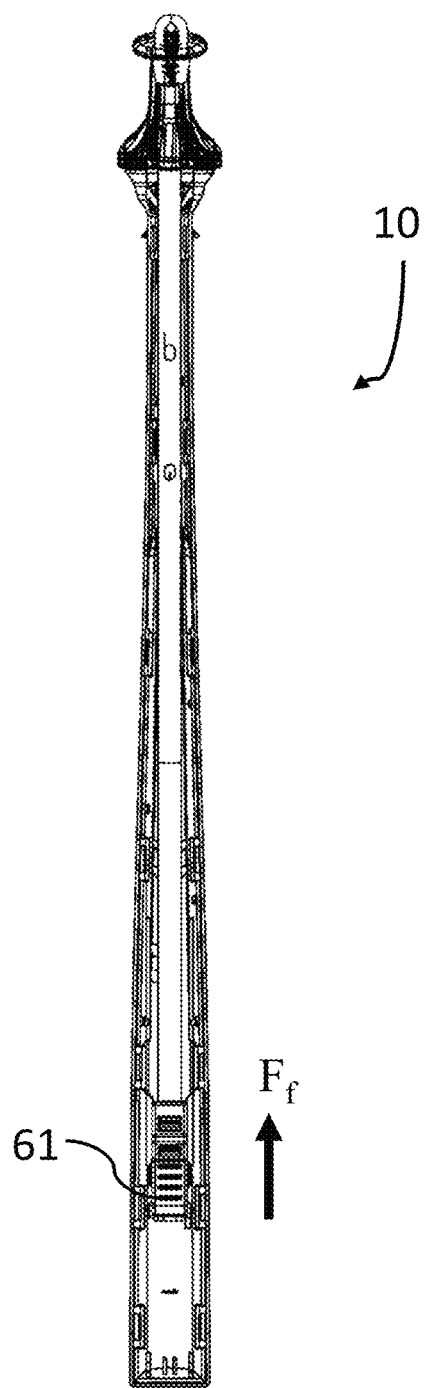
Figure 15G:
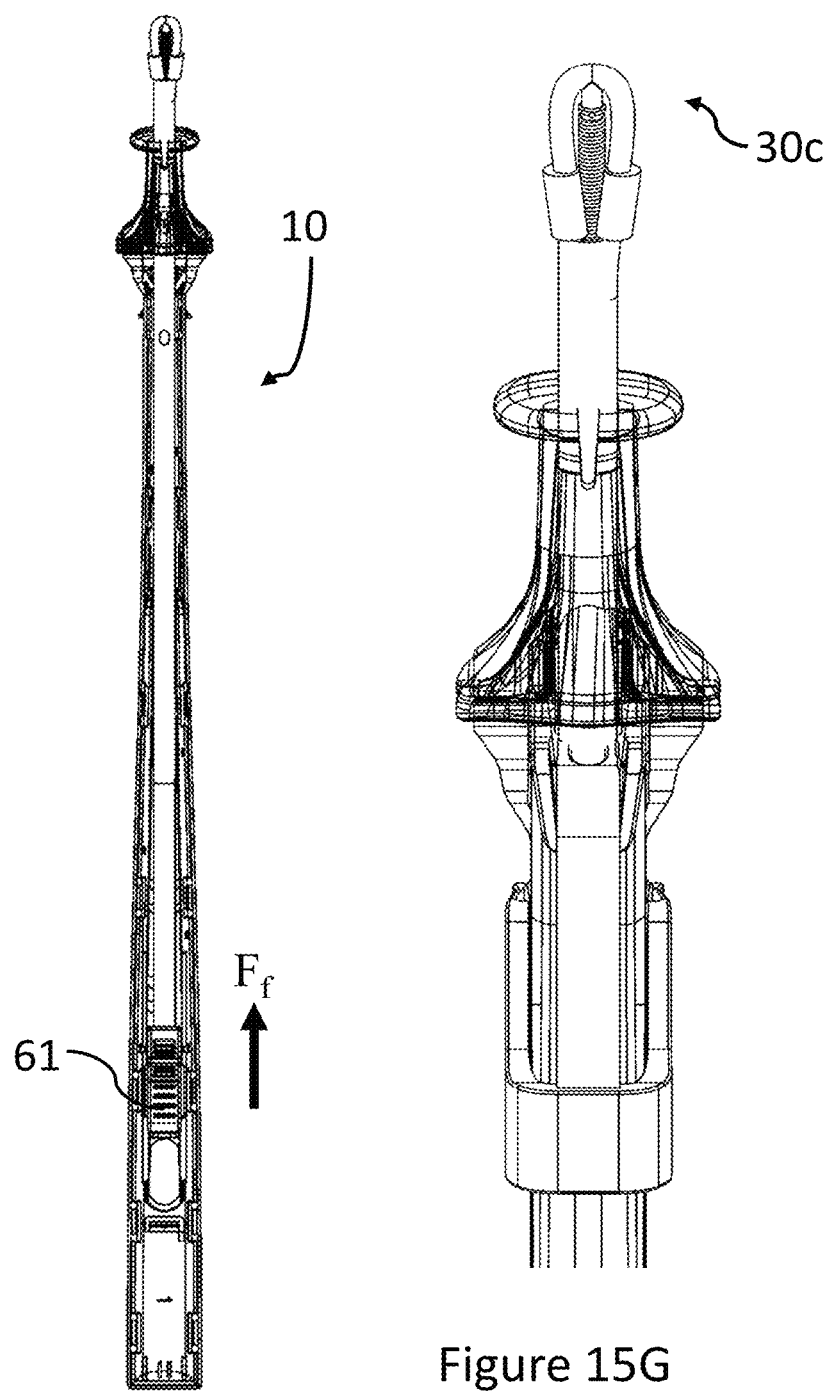
Figure 15H:
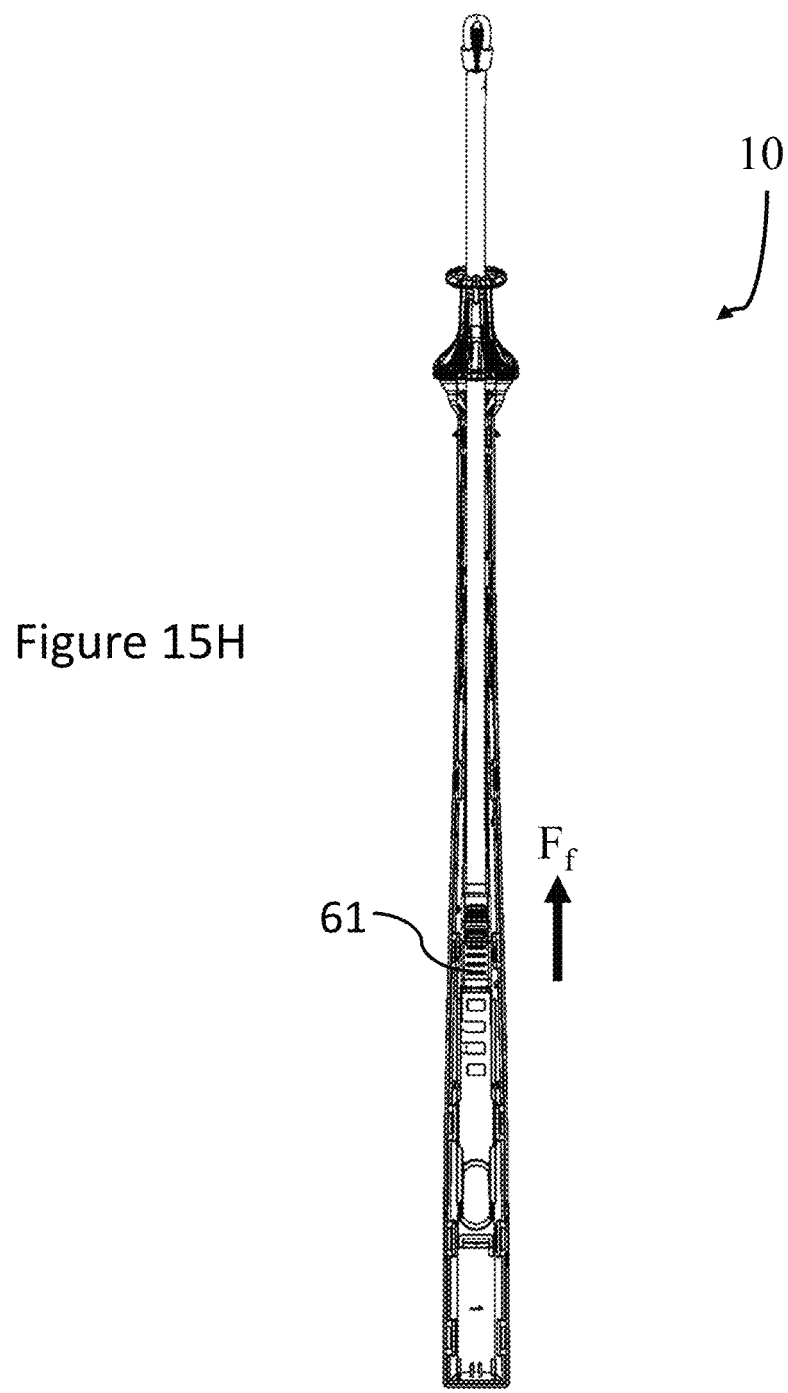
Figure 15J:
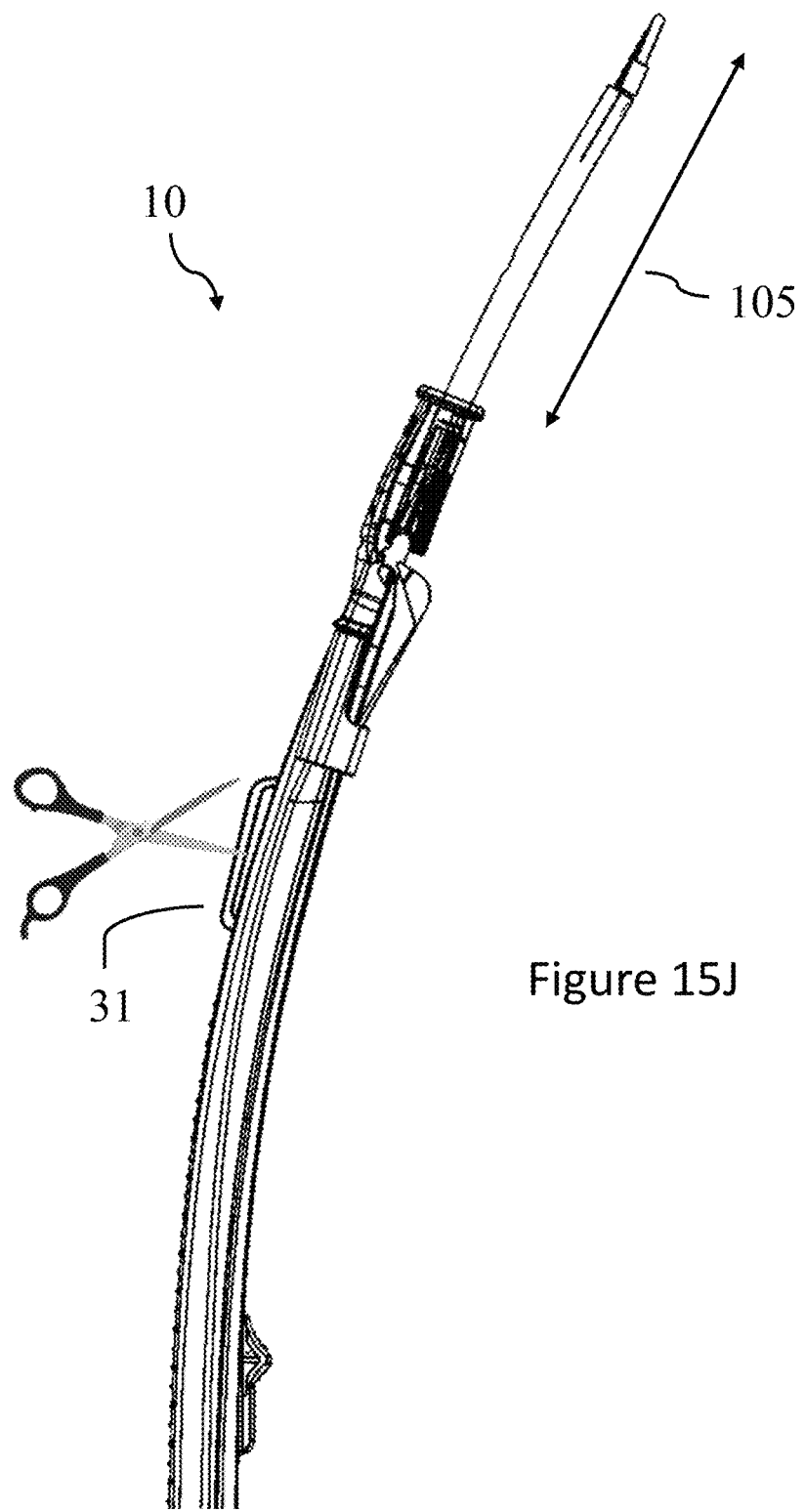
Figure 15K:
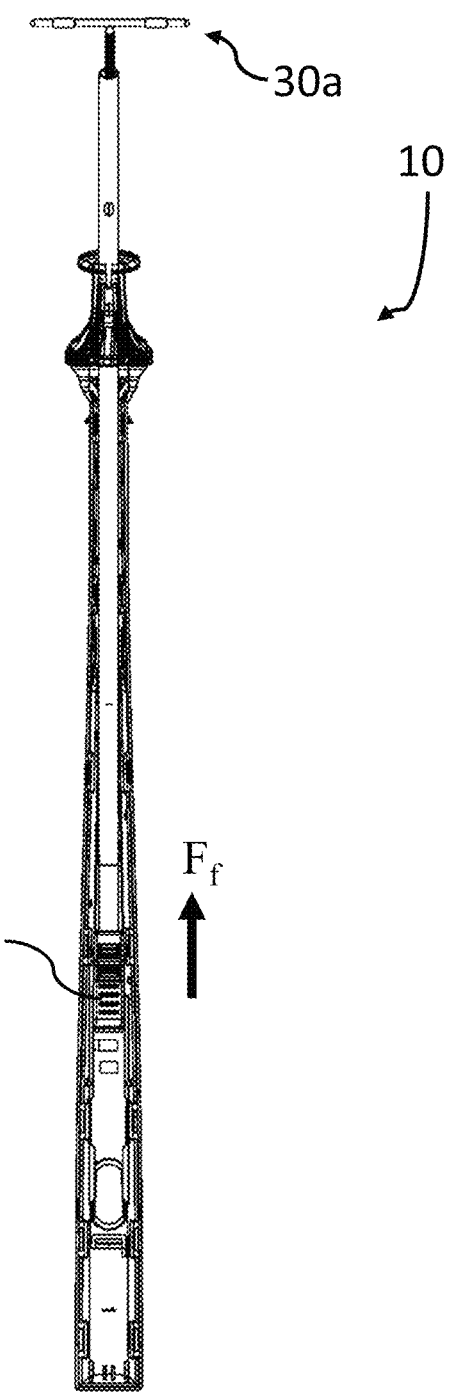
Figure 15L:
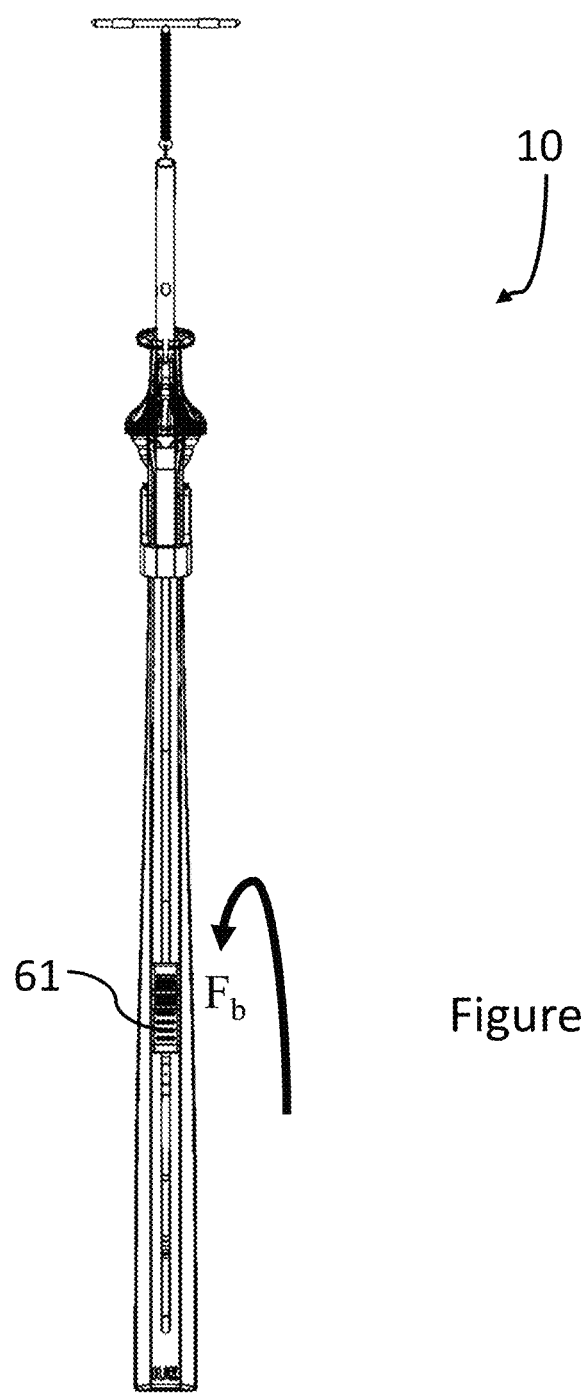
Figure 16:
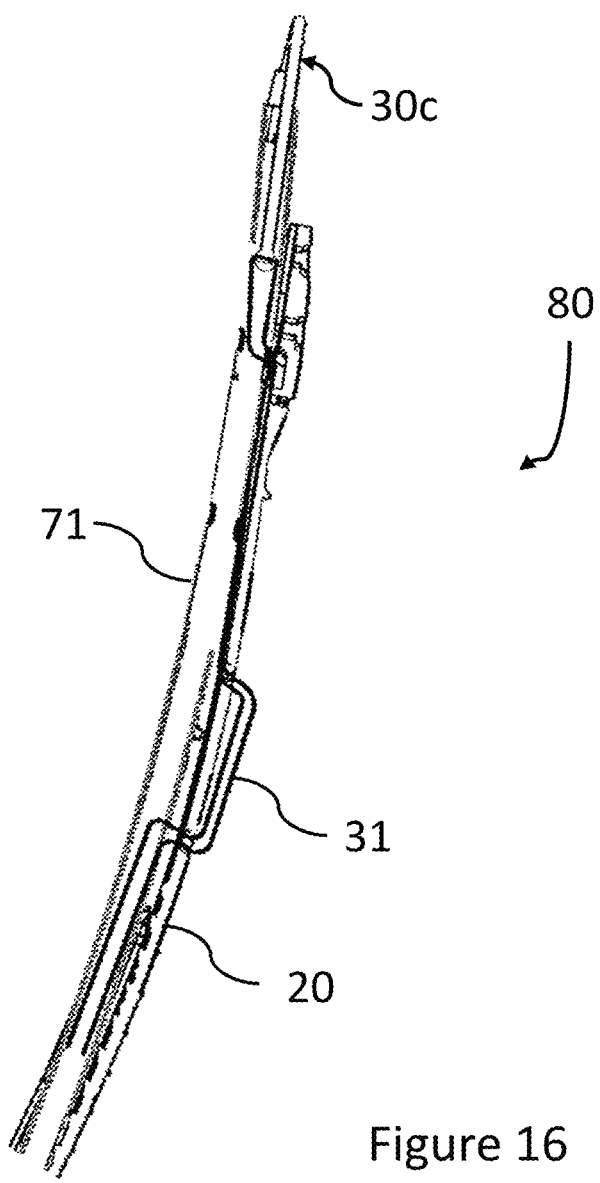
FIG. 16 is a partial sectional view of a string management arrangement.

FIG. 12B-12C, the instrument (10) is assembled as follows:
Pressing the reversibly collapsible projections pair (44) of the open converger (40) against the corresponding receptacles (25) of the base (20),
Inserting completely a non-graduated end of the graduated tube (71) in the tube receptacle (65) of the bidirectional carrier (61) till the back face (70) is reached, FIG. 6,
Inserting the latching rod (81) from its IUD end (5) in the graduated tube (71) through the open end of the tube receptacle (65) of the bidirectional carrier (61) till the pair of locking teeth (67) locks into the second pair of seats (86) of the latching rod (81),
Widening the slot (56) temporarily, FIG. 12A, as the travel ways (69A) on either side of the interfacing wall (69) of the bidirectional carrier (61) engulfs the flat runway (57) on either side of the slot (56) of the navigator (50),
Pulling back the bidirectional carrier (61) positioning it between the two guide walls (58), FIG. 12B,
Inserting the string (31) of the IUD in the graduated tube (71) and taking the string out of the exit hole (73) of the graduated tube (71), FIG. 16,
Inserting the stem (33) of the IUD (30) through the divergence (55) of the navigator (50) into the graduated tube (71) till the lower end (37) of the stem (33) sits on the conical seat (82) having two resting points (83) on the latching rod (81), while the knot (38) of the string (31) may either sit in the knot room (84) on the delatching rod (81) or the knot (38) may remain suspended in the graduated tube (71),
Taking out the string (31) from the outpoint (87) on the floor (22) of the base (20),
Inserting the aligner plug (51A) of the navigator (50) in the alignment socket (51B) of the open converger (40),
Pressing the mirror symmetrical fences (52) of the navigator (50) so as to engage the plurality of complementary lockable windows (7B) of the navigator (50) with the corresponding plurality of locking projections (7A) of the base (20), and
Inserting the string (31) in the inpoint (88) on the floor (22) of the base (20).
Pressing the elongated grips (93) of the gated support (90) over the navigator (50) near the IUD end (5), the leafy arm (91) flexing upwards, the end points (96) of the inverted "U" gate (95) sitting on the graduated tube (71)
Sliding the gated support (90) towards the platform of the base (20) till the elongated grip (93) is obstructed by the collar (29), the graduated tube (71) ends, allowing the sloped edges (97) to slide down an edge of the graduated tube (71), the leafy arm (91) to spring back and flex downwards, the downward fork (94) forming the inverted "U" gate (95) surrounding the stem (33) of the IUD (30), FIG. 15A, as the assembly is completed, the arms of the IUD (30) sit on the platform (23) of the floor (22) of the base (20).

Figure 13:
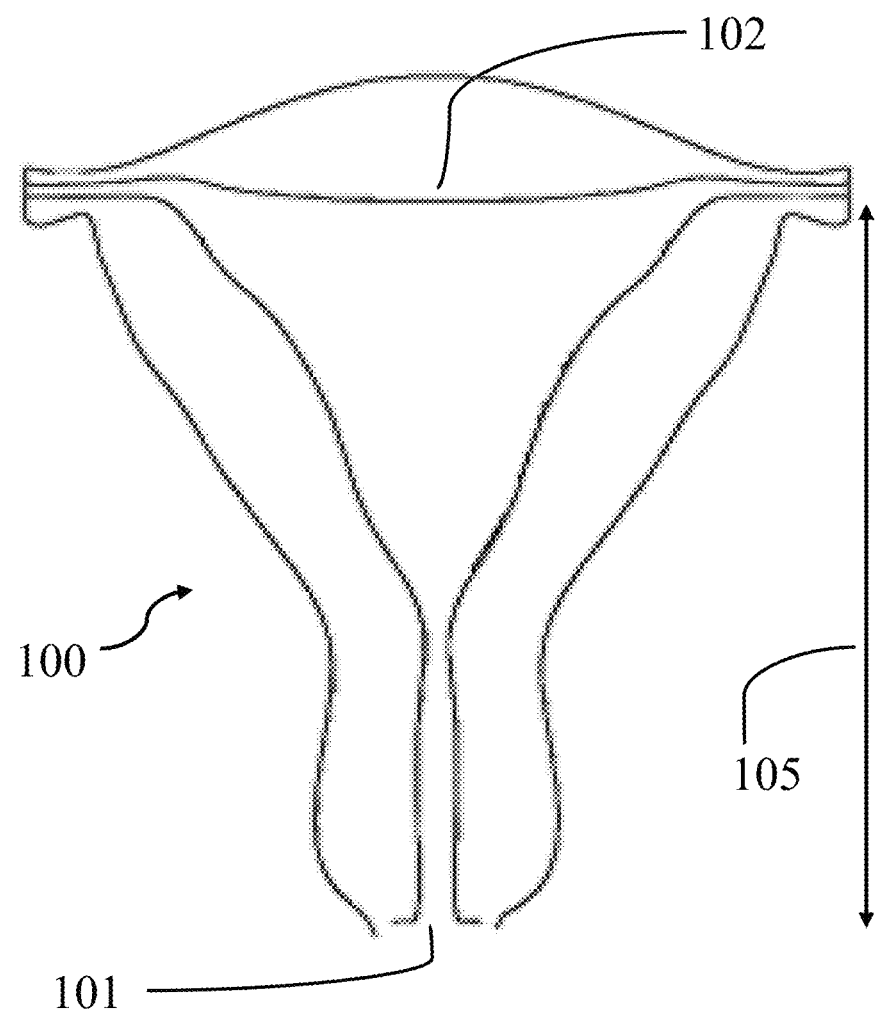
FIG. 13 is a simplified sketch of a uterus.

FIG. 13-14, any IUD placed properly in uterus (100) of a woman ought to sit closest to fundus (102) of uterus, and strings ought to be long enough to hang out of the cervical os (101) by a check length (106) about 3 to 5 cm, so that while woman can just feel presence of IUD by feeling its strings by inserting her finger(s) in her uterus, the string(s) should not cause discomfort to her partner during intercourse. A uterine depth (105), that is a measure from fundus (102) to cervical os (101) of different woman illustratively varies between 4 cm to 10 cm. IUD (30) supplied with the instrument (10) as per present invention has a string (31) long enough to meet the medical requirement described above for all sizes, and excess length of string (31) is trimmed away during or after insertion and placement of IUD (30) in uterus (100). Before starting insertion procedure, the medical service providers measure a uterine depth (105) by known methods.

FIGS. 15A-15L, a method to load the instrument (10) as per present invention and safely place the IUD (30) in uterus (100) comprises the steps of:
a) Sounding a uterus of woman and determining a uterine depth (105),
b) Sliding the bidirectional carrier (61) towards the IUD end (5) by medical service provider placing his or thumb on the push zone (62) and applying a forward force $F_f$ on the cliff (64), the graduated tube (71) along with the latching rod (81) pushing the lower end (37) of the stem (33) of the IUD (30), the inverted "U" gate (95) supporting the stem from both sides and preventing a buckling of the stem (33) of the ID (30), and the arms (34) of the IUD (30) folding down, c) Further sliding the bidirectional carrier (61) towards the IUD end (5) by medical service provider continuing placing his or thumb on the push zone (62) and further applying the forward force $F_f$ on the cliff (64), the downward projection (85) of the latching rod (81) getting obstructed by the delatcher (26) on the base (20), resultantly the pair of locking teeth (67) of the bidirectional carrier (61) getting delatched from the second pair of seats (86B) and getting latched with the first pair of seats (86A) of the latching rod (81), the edge of the graduated tube (71) pushing up the sloped edges (97), lifting up of the inverted "U" gate (95), sliding of only the graduated tube (71) on the stem (33) by the measure of length (89), and engulfing a part of arms (34) of the IUD (30), d) Further sliding the bidirectional carrier (61) towards the IUD end (5) by medical service provider continuing placing his or thumb on the push zone (62) and further applying the forward force $F_f$ on the cliff (64), the graduated tube (71) along with the latching rod push (81) the lower end (37) of the stem (33) of the IUD (30) till the graduated tube (71) with a folded IUD (30) emerges out from the flange (45) by the measure of the uterine depth (105), e) Trimming the string (31) in-between the outpoint (87) and the inpoint (88) of the instrument (10)

f) Sliding backward sliding the bidirectional carrier (61) towards the operator end (6) by the medical service provider placing his or thumb on the pullback zone (63) and applying a backward force Fb on the cliff (64), pulling back the graduated tube (71) along with the latching rod (81) from over the stem (33) of the IUD (30), g) Applying a force (Fbr) by thumb on the open converger (40), separating a part of the base (20) carrying the open converger (40), rendering the instrument (10) non-reusable irreversibly.

The step (f) is performed after inserting the graduated tube (71) in the uterus (100) till the flange (45) touches the cervical os (101), thereby releasing the IUD (30) in the uterus (100) with the arms (34) of the IUD (30) next to fundus (102). Step (g) is performed after withdrawing the instrument (10) from vaginal cavity of woman.

I claim:

1. An instrument (10) to downfold an intrauterine device (30) having identical arms (34), a stem (33) and a string (31), the instrument (10) comprising:

a base (20) having a floor (22) with a delatcher (26), an outside of the base (20) having a collar (29);

a navigator (50) having an aligner plug (51A), two mirror symmetrical fences (52) along an entire length of the navigator (50), joining together atthe operator end (6), thereby forming a slot (56) with a divergence (55);

an open converger (40) having a flange (45), a covered channel (41) commencing with a circular opening (41a) and transitioning to a funneling opening (41b) symmetrical about an imaginary orthogonal plane passing through a line X-X', the funneling opening (41b) diverging to two dome shaped openings (43), a reversibly collapsible projections pair (44), an alignment socket (51B);

a driver assembly (60) having a bidirectional carrier (61), a graduated tube (71), and a latching rod (81); and a gated support (90) having a leafy arm (91) and a downward fork (94) forming an inverted "U" gate (95) having sloped edges (97) with end points (96), at the other end, a holder (92) having an elongated grip (93) on either side;

wherein the reversibly collapsible projections pair (44) of the open converger (40) press-fits against corresponding receptacles (25) of the base (20), the aligner plug (51A) of the navigator (50) inserts in the alignment socket (51B) of the open converger (40), a lower end (37) of the stem (33) of the intrauterine device (30) sits on a conical seat (82) having two resting points (83) on the latching rod (81), while a knot (38) of the string (31) sits in a knot room (84) on the latching rod (81).

2. The instrument (10) to downfold an intrauterine device (30) of claim 1, wherein the floor (22) of base (20) has two walls (21), the floor (22) narrowing towards an intrauterine device end (5), widening again to form a platform (23), and converging to a supporting zone (24) having at least a receptacle (25), till the intrauterine device end (5).

3. The instrument (10) to downfold an intrauterine device (30) of claim 1, wherein the base (20) has a weakening combination (19) comprising a pair of weakening notches (19a) and at least a depleted zone (19b) on the platform (23) of the base (20), wherein a human force ($F_{br}$) breaks the floor (22) from the weakening notches (19a), separating a part of the base (20) carrying the open converger (40).

4. The instrument (10) to downfold an intrauterine device (30) of claim 1, wherein the base (20) has a string management arrangement (80) comprising at least one outpoint (87) and one inpoint (88) on the floor (22) of the base (20), the string (31) exits from the outpoint (87) and re-enters from the inpoint (88), the outpoint (87) is at a trim length (46) while the inpoint (88) is at a conservative length (47), a scale (48) provided alongside.

5. The instrument (10) to downfold an intrauterine device (30) in claim 1, wherein the covered channel (41) of the open converger (40) has an additional room (42) towards an upper side.

6. The instrument (10) to downfold an intrauterine device (30) of claim 1, wherein the bidirectional carrier (61) has a push zone (62) and a pullback zone (63), separated by a cliff (64) on an upper side (66), a tube receptacle (65) on a lower side (68) and a pair of locking teeth (67) with a back face (70) integrated to an open end of the tube receptacle (65), the upper side (66) and the lower side (68) joined by an interfacing wall (69) between a bottom side of the push zone (62)+the pullback zone (63) and an upper side (66) of the tube receptacle (65), forming travel ways (69A) on either side of the interfacing wall (69).

7. The instrument (10) to downfold an intrauterine device (30) of claim 1, wherein the graduated tube (71) has a plurality of sounding markings (72).

8. The instrument (10) to downfold an intrauterine device (30) in claim 1, wherein the graduated tube (71) has at least an exit hole (73) and optionally an entry hole (74).

9. The instrument (10) to downfold an intrauterine device (30) of claim 1, wherein the latching rod (81), has a conical seat (82) having two resting points (83) and a knot room (84), reserved for the knot (38) of the string (31) of the intrauterine device (30), a progressively increasing cylindrical portion, a first pair of seats (86A), again progressively increasing to a second pair of seats (86B), and a downward projection (85), the first pair of seats (86A) at a measure of length (89) with respect to the second pair of seats (86B).

10. The instrument (10) to downfold an intrauterine device (30) of claim 1, wherein the mirror symmetrical fences (52) of the navigator (50) have a user side (53) and a concealed side (54), the user side (53) having a flat runway (57) on either side of the slot (56), the concealed side (54) has a guide wall (58) on either side of the slot (56) and a plurality of complementary lockable windows (7B) all along an external edge of both mirror symmetrical fences (52), and wherein consequent to a slender shapeof the navigator (50) the slot (56) can be widened temporarily.

11. A method to load an instrument (10) and configure to safely place an intrauterine device (30) in uterus (100), the method comprises the steps of:

a) sounding a uterus of a woman and determining a uterine depth (105);

b) sliding a bidirectional carrier (61) of a driver assembly (60) towards an intrauterine device end (5) by a medical service provider placing his or her thumb on a push zone (62) of the bidirectional carrier (61) and applying a forward force ($F_f$) on a cliff (64), a graduated tube (71) along with a latching rod (81) pushing a lower end (37) of a stem (33) of the intrauterine device (30), an inverted "U" gate (95) supporting the stem (33) from both sides and preventing a buckling of the stem (33) of the intrauterine device (30), and arms (34) of the intrauterine device (30) folding down;

c) further sliding the bidirectional carrier (61) towards the IUD end (5) by the medical service provider continuing placing his or her thumb on the push zone (62) and further applying the forward force ($F_f$) on the cliff (64), a downward projection (85) of the latching rod (81) getting obstructed by a delatcher (26) on a base (20), resultantly a pair of locking teeth (67) of the bidirectional carrier (61) getting delatched from a second pair of seats (86B) and getting latched with a first pair of seats (86A) of the latching rod (81), an edge of the graduated tube (71) pushing up sloped edges (97), lifting up of the inverted "U" gate (95), sliding of only the graduated tube (71) on the stem (33) by a measure of length (89), and engulfing a part of the arms (34) of the intrauterine device (30);

d) further sliding the bidirectional carrier (61) towards the intrauterine device end (5) by the medical service provider continuing placing his or her thumb on the push zone (62) and further applying the forward force ($F_f$) on the cliff (64), the graduated tube (71) along with the latching rod (81) push the lower end (37) of the stem (33) of the intrauterine device (30) till the graduated tube (71) with a folded intrauterine device (30c) emerges out from a flange (45) by a measure of the uterine depth (105);

e) trimming a string (31) in-between an outpoint (87) and an inpoint (88) of the instrument (10);

f) sliding backward the bidirectional carrier (61) towards an operator end (6) by the medical service provider placing his or her thumb on the pullback zone (63) and applying a backward force ($F_b$) on the cliff (64), pulling backthe graduated tube (71) along with the latching rod (81) from over the stem (33) of the intrauterine device (30); and g) applying a force ($F_{br}$) by the thumb on an open converger (40), separating a part of the base (20) carrying the open converger (40), rendering the instrument (10) non-reusable irreversibly.

12. The method of claim 11, wherein the instrument (10) is configured for the sliding backward of the bidirectional carrier (61) after inserting the graduated tube (71) in the uterus (100) till the flange (45) touches the cervical os (101), releasing the intrauterine device (30) in the uterus (100) with the arms (34) of the intrauterine device (30) next to fundus (102).

13. The method of claim 11, wherein the instrument (10) is configured for separating a part of the floor (22) by applying a force ($F_{br}$) on the open converger (40) after withdrawing the instrument (10) from vaginal cavity of the woman.

* * * * *